US012721926B2

(12) United States Patent
Rong et al.

(10) Patent No.: US 12,721,926 B2
(45) Date of Patent: Sep. 1, 2026

(54) MEDICAL ARTICLE WITH BACKING

(71) Applicant: Solventum Intellectual Properties Company, Maplewood, MN (US)

(72) Inventors: Haoming Rong, Woodbury, MN (US); Vinod P. Menon, Woodbury, MN (US); Linda Kay Metzger Olson, St. Paul, MN (US)

(73) Assignee: Solventum Intellectual Properties Company, Eagan, MN (US)

( * ) Notice: Subject to any disclaimer, the term of this patent is extended or adjusted under 35 U.S.C. 154(b) by 1293 days.

(21) Appl. No.: 17/309,493

(22) PCT Filed: Dec. 20, 2019

(86) PCT No.: PCT/IB2019/061198

§ 371 (c)(1),
(2) Date: Jun. 1, 2021

(87) PCT Pub. No.: WO2020/129009

PCT Pub. Date: Jun. 25, 2020

(65) Prior Publication Data

US 2022/0040369 A1 Feb. 10, 2022

Related U.S. Application Data

(60) Provisional application No. 62/783,368, filed on Dec. 21, 2018.

(51) Int. Cl.

| | |
|---|---|
| ***A61L 15/58*** | (2006.01) |
| ***A61F 13/02*** | (2024.01) |
| ***A61L 15/44*** | (2006.01) |
| ***A61L 15/46*** | (2006.01) |

(52) U.S. Cl.
CPC .......... *A61L 15/58* (2013.01); *A61F 13/0259* (2013.01); *A61L 15/44* (2013.01); *A61L 15/46* (2013.01)

(58) Field of Classification Search
CPC .......... A61L 15/58; A61L 15/44; A61L 15/46; A61L 15/26; A61L 2300/206; A61L 2300/404; A61L 31/141; A61L 31/14; A61L 31/16; A61F 13/0259; C08L 33/10
See application file for complete search history.

(56) References Cited

U.S. PATENT DOCUMENTS

| | | | | |
|---|---|---|---|---|
| RE24,906 | E | 12/1960 | Ulrich | |
| 4,049,483 | A | 9/1977 | Loder | |
| 4,051,853 | A | 10/1977 | Egan, Jr. | |
| 4,381,380 | A * | 4/1983 | LeVeen | A61L 15/26 521/905 |
| 4,472,480 | A | 9/1984 | Olson | |
| 4,595,001 | A | 6/1986 | Potter | |
| 4,643,181 | A | 2/1987 | Brown | |
| 5,717,005 | A | 2/1998 | Richardson | |
| 6,680,113 | B1 * | 1/2004 | Lucast | A61F 13/023 602/903 |
| 9,713,659 | B2 | 7/2017 | Menon | |
| 2004/0082897 | A1 | 4/2004 | Rangel | |
| 2008/0000003 | A1 | 1/2008 | Melander | |
| 2008/0287538 | A1 | 11/2008 | Scholz et al. | |
| 2011/0290259 | A1 | 12/2011 | McGuire, Jr. et al. | |
| 2015/0238444 | A1 | 8/2015 | Menon | |
| 2015/0250931 | A1 * | 9/2015 | Bharti | A61M 27/00 604/319 |
| 2015/0299918 | A1 * | 10/2015 | Kumihiro | D01F 8/06 442/329 |
| 2015/0328360 | A1 | 11/2015 | Menon | |
| 2015/0367021 | A1 | 12/2015 | Wibaux | |
| 2016/0296678 | A1 * | 10/2016 | Menon | A61L 31/14 |
| 2017/0000659 | A1 | 1/2017 | Autran | |
| 2017/0043450 | A1 * | 2/2017 | Graham | B24D 3/002 |

FOREIGN PATENT DOCUMENTS

| | | | |
|---|---|---|---|
| WO | WO-2009088894 A2 * | 7/2009 | A01N 25/02 |
| WO | WO 2010-080936 | 7/2010 | |
| WO | WO 2014-035981 | 3/2014 | |

OTHER PUBLICATIONS

Supplemental European Search Report for Application 1989881 dated Jul. 28, 2022, 2 pages.
Noller, "Chemistry of Organic Compounds, Chapter 6 Alkyl Halides Grignard reagents", Journal of chemical education, 1957, pp. 121-122.
Satas, "Handbook of Pressure Sensitive Adhesive Technology", Van Nostrand Reinhold, 1989, Ed.02, pp. 172-173.
International Search report for PCT International Application No. PCT/IB2019/061198 mailed on Apr. 24, 2020, 3 pages.

* cited by examiner

*Primary Examiner* — Snigdha Maewall

(57) ABSTRACT

Aspects of the present disclosure relate to an article that includes a conformable backing having first and second opposed major surfaces. The conformable backing can be formed from a thermoplastic polymer selected from a group consisting of polyurethanes, polyesters, and combinations thereof. The conformable backing has a tensile strength of no greater than 60 grams per centimeter force at 25% elongation in a machine direction according to the Tensile and Elongation Test Method. A hydrophobic adhesive can be disposed on a portion of the first major surface of the conformable backing. The hydrophobic adhesive includes a cationic, bioactive agent, a hydrophobic solubilizer capable of solubilizing at least part of the bioactive agent, and a hydrophobic plasticizing agent having a weight average molecular weight of above 1500.

15 Claims, 13 Drawing Sheets

MEDICAL ARTICLE WITH BACKING

CROSS REFERENCE TO RELATED APPLICATIONS

This application is a national stage filing under 35 U.S.C. 371 of PCT/IB2019/061198, filed Dec. 20, 2019, which claims the benefit of Provisional Patent Application No. 62/783,368, filed Dec. 21, 2018, the disclosure of which is incorporated by reference in its/their entirety herein.

BACKGROUND

Antiseptic is commonly used for routine preoperative skin cleansing of the surgical site to reduce the microbial load on the patient's skin surface. Several antiseptic agents are available for preoperative skin preparation including alcohol and chlorhexidine or iodine/iodophors as antiseptic agents.

The patient's skin is a significant source of potential infectious microorganisms such as *Staphylococcus aureus* and coagulase-negative staphylococci, which are becoming increasingly resistant to antibiotics and account for more than a third of all surgical wound infections. Surgical prep alone may have difficulty eliminating bacteria that continuously regenerate after prepping. The bacteria left behind can migrate into the surgical wound, increasing the risk for wound contamination and infection.

Surgical incise drapes with antiseptic agents have been available using iodine/iodophors such as Ioban by 3M (St. Paul, MN). Some patients have iodine sensitivities making alternative antiseptic agents such as chlorhexidine digluconate (CHG) desirable. However, these antiseptic agents have had limited skin adhesion when incorporated into drapes, particularly when combined with a film-forming composition (e.g., a surgical prep).

SUMMARY

Aspects of the present disclosure relate to an article that includes a conformable backing having first and second opposed major surfaces. The conformable backing can be formed from a thermoplastic polymer selected from a group consisting of polyurethanes, polyesters, and combinations thereof. The conformable backing has a tensile strength of no greater than 60 grams per centimeter force at 25% elongation in a machine direction according to the Tensile and Elongation Test Method. A hydrophobic adhesive can be disposed on a portion of the first major surface of the backing. The hydrophobic adhesive includes a cationic, bioactive agent, a hydrophobic solubilizer capable of solubilizing at least part of the bioactive agent, and a hydrophobic plasticizing agent having a weight average molecular weight of above 1500.

Additional aspects include a system that includes the article. The article can be a medical device such as a surgical drape and also include an antiseptic solution comprising alcohol. When the first side of the article contacts a layer of the antiseptic solution applied to a topographical surface, then a frequency of lift of any portion of the article can be no greater than 80% out of a statistically relevant sample set of topographical surfaces.

Additional aspects also include a method of making the article and a method of using the article with a film-forming antiseptic composition.

DETAILED DESCRIPTION

It has been found that the conformability of the thermoplastic polymeric film backing is highly correlated with incise drape lift on prepped skin under wet challenge conditions. The drape lift on prepped skin under wet challenge can be significantly reduced by using a more conformable thermoplastic polymeric film backing.

Aspects of the present disclosure relate to an article having conformability over topographical surfaces. More particularly, aspects of the present disclosure relate to medical articles having conformability to anatomical surfaces of a patient. The conformability can be the result of selecting a polymer for a backing having a shore A hardness rating of no greater than 75 which results in the backing having a tensile strength of no greater than 200 grams-force at 25% elongation in the machine direction. In other aspects, the article can minimize lifting when combined with the film-forming composition.

Figure 1A:
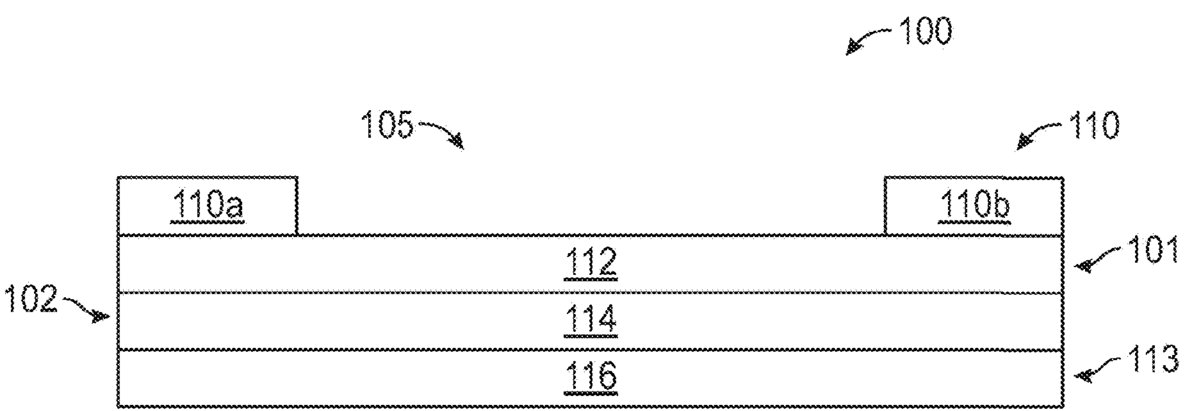
FIGS. 1A-1C illustrate an article that adheres to topographical surfaces, according to an aspect of the present disclosure.
Figure 1B:
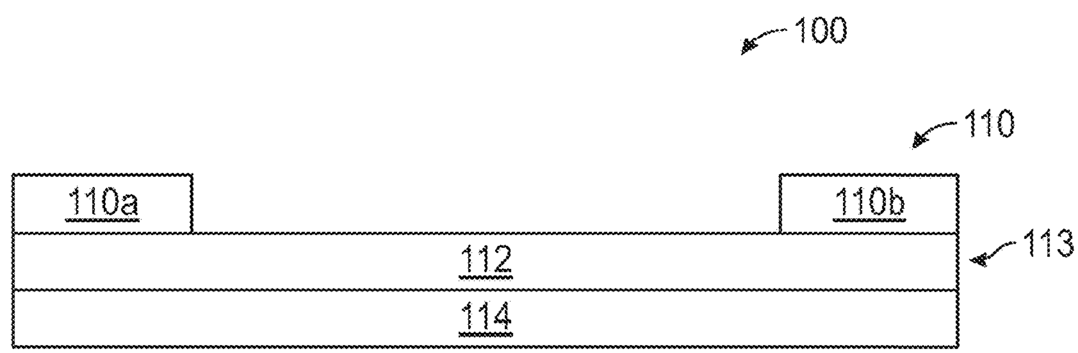

FIGS. 1A-1B illustrate an article 100. The article 100 can be a medical article such as a drape, wound dressing, or the like. In at least one embodiment, the article 100 is an incise drape that may be useful in surgical procedures.

The article 100 can include a conformable backing 112, an adhesive 114, and optionally, a support layer 110 and release liner 116. The adhesive 114 can be disposed on the conformable backing 112 to form an article with properties that allow the article 100 to adhere to topographical surfaces such as animal anatomical joints. When the joint is flexed and then returned to its unflexed position, the backing 112 can be made such that it stretches to accommodate the flexion of the joint, but is resilient enough to continue to conform to the joint when the joint is returned to its unflexed condition. The backing 112 is generally conformable to anatomical surfaces. As such, when the backing 112 is applied to an anatomical surface, it conforms to the surface even when the surface is moved.

The backing 112 may be cast (e.g., from solvent or water) or extruded. While various thicknesses of backing 112 are possible depending on a selection of polymer material, the backing 112 can have an average thickness from 0.5 to 2 mils. (12.7 microns to 50.8 microns) (inclusive), preferably 0.7 mils to 1.2 mils (18 microns to 30 microns) (inclusive), more preferably 0.8 mils to 1.2 mils (20 microns to 30 microns) (inclusive) as calculated using ASTM D6988-13.

In at least one embodiment, the backing 112 may be unitary; that is, it may consist of a single layer. In certain embodiments, the backing 112 may be a composite backing. Typically, the backing is at least substantially homogeneous, although this is not a requirement. The backing 112 may be perforated; however, if perforated, the average thickness is not determined using areas of the perforations where the thickness would, of course, be zero as no backing 112 is present there.

In at least one embodiment, the backing 112 can transmit moisture vapor at a rate equal to or greater than human skin as measured using ASTM E96BW. In one example, the moisture vapor transmission rate of the backing alone can be at least 400 $g/m^2/24$ hours, and preferably between 500 and 3500 $g/m^2/24$ hours. Preferably, the backing 112 is impermeable to liquid water and substantially free of void space, although minor amounts of porosity may be acceptable. For example, the backing may have less than 10 percent, less than 2 percent, less than 1 percent, or even less than 0.01 percent of intrinsic voids (i.e., voids that are not deliberately added, but are an intrinsic property of the material making up the backing), based on the total volume of the backing.

The backing 112 can be formed from thermoplastic polymers. The thermoplastic polymers can include polyurethanes, polyesters, polyamides, polyolefins, styrene block copolymers, and combinations thereof.

In at least one embodiment, the backing 112 can be formed from thermoplastic polyurethane, co-polyester, or polyether block amide films. These films combine the desirable properties of resiliency, high moisture vapor permeability, and transparency found in backings.

In at least one embodiment, the backing may comprise one or more polyurethanes. In embodiments, the polyurethane comprises, or at least consists essentially of, at least one thermoplastic polyurethane (TPU). The term "consisting essentially of" as used in this context means that additive compounds (e.g., fragrances, colorants, dyes, antioxidants, flame retardants, melt processing aids, UV light stabilizers, and/or fillers) may be present in the backing as long as tensile strength and ultimate elongation remains substantially unaffected by their presence. For example, the additives may have less than a 5 percent, or preferably less than 1 percent effect on tensile strength and ultimate elongation.

In at least one embodiment, the backing 112 may comprise a single thermoplastic polyurethane or a combination of thermoplastic polyurethanes.

Thermoplastic polyurethanes are well known and can be made according to many known techniques, or they may be obtained for commercial suppliers. For example, Lubrizol Corp., Cleveland, Ohio, is one commercial supplier of various thermoplastic polyurethanes such as, for example: polyester-based aromatic TPUs available under the trade designation "ESTANE GP TPU (B series)" (e.g., grades 52 DB, 55 DB, 60 DB, 72 DB, 80 AB, 82A, 85 AB, and 95 AB); and polyester and polyether based TPU s available under the trade designation "ESTANE 58000 TPU series" (e.g., grades 58070, 58091, 58123, 58130, 58133, 58134, 58137, 58142, 58144, 58201, 58202, 58206, 58211, 58212, 58213, 58215, 58219, 58226, 58237, 58238, 58244, 58245, 58246, 58248, 58252, 58271, 58277, 58280, 58284, 58300 (or EZ10, 58309, 58311, 58315, 58325, 58370, 58437, 58610, 58630, 58810, 58863, 58881, and 58887).

In another example, BASF (Wyandotte, Michigan) is another commercial supplier of various polyester and polyether-based thermoplastic polyurethanes available under the trade designation "Elastollan" e.g., the 800 Series, including ET 870, 880AN.

The backing 112 or any component can also be defined by one or more properties. For example, a homopolymer material formed from the thermoplastic polymer can have has a shore A hardness rating of no greater than 85, no greater than 80, no greater than 78, no greater than 76, no greater than 75, no greater than 74, no greater than 73, no greater than 72, no greater than 71, or no greater than 70.

The backing 112 can also have a modulus of elasticity no greater than the Dahlquist criterion, i.e., $10^5$ Pa, at a temperature within a range of from about 25° C. to about 80° C., and (ii) a modulus less than the Dahlquist criterion at a temperature greater than 100° C. Details concerning the Dahlquist criterion are known in the adhesive arts and are described in the Handbook of Pressure Sensitive Adhesive Technology, Donatas Satas (Ed.), 2nd Edition, pp. 172-173, Van Nostrand Reinhold, New York, NY (1989). These moduli are storage moduli and are measured via dynamic mechanical analysis (DMA) as known in the art.

In at least one embodiment, the backing 112 has a tensile strength of no greater than 200 grams force per centimeter, no greater than 150 grams force per centimeter, no greater than 100 grams force per centimeter, no greater than 60 grams force per centimeter, or no greater than 50 grams force per centimeter at 25% elongation in the machine direction as measured in the Tensile and Elongation Test method described herein. In at least one embodiment, the backing 112 can have a tensile strength of between 40 grams force per centimeter and 5 grams force per centimeter (inclusive) at 25% elongation in the machine direction as measured in the Tensile and Elongation Test method described herein.

In at least one embodiment, the backing 112 can have a Young's modulus between 5 and 20 MPa(inclusive), preferably between 8 and 12 MPa(inclusive), and most preferably between 8 and 10 MPa (inclusive).

In at least one embodiment, the article 100 can include an optional support layer 110, or carrier. The material used to form the support layer 110 is generally substantially more rigid than the backing 112 to prevent the backing 112 from improperly wrinkling during application to a patient. In general, the support layer 110 materials can include, but are not limited to, an elastic film, a non-elastic film, non-woven fibrous web, woven fibrous web, knits, and polyethylene/vinyl acetate copolymer-coated papers and polyester films. FIG. 1A illustrates two support layer 110*a*, 110*b* structures that are disposed proximate to a perimeter 106.

Figure 1C:
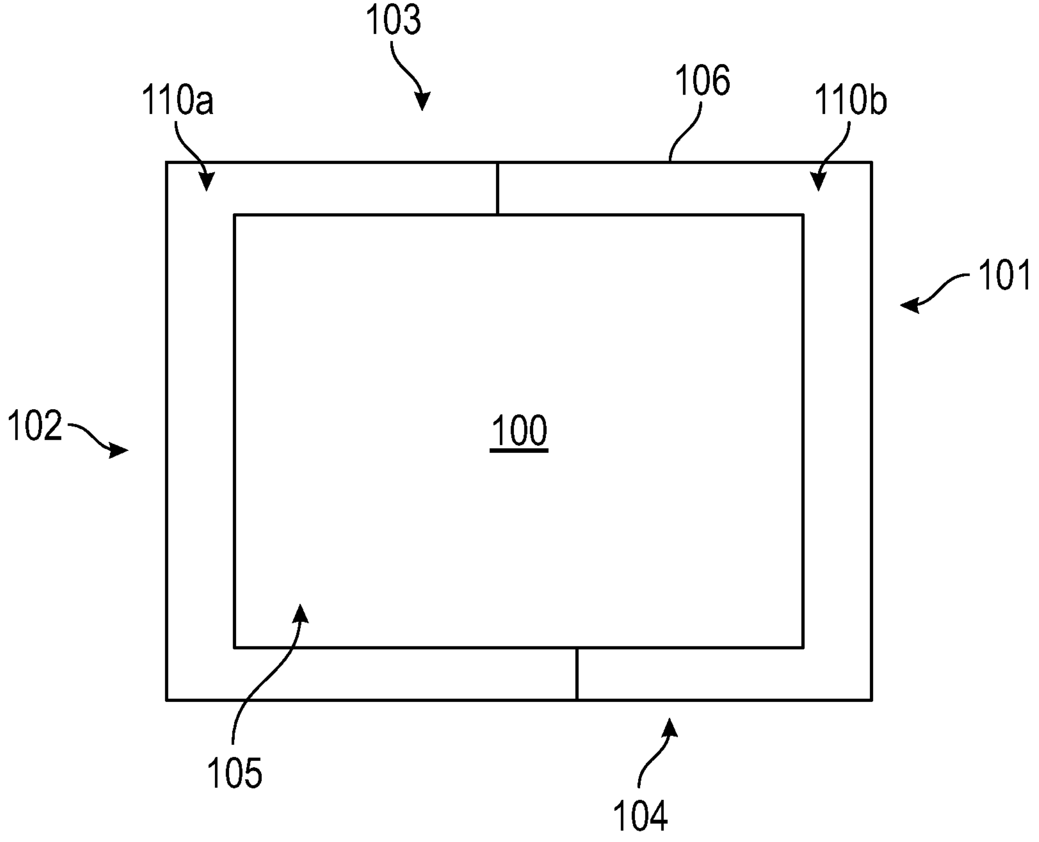

In at least one embodiment, the support layer 110 is permanently adhered or attached to the backing 112 either directly or by an adhesive 114. The support layer can be formed by cutting the support layer in the desired pattern and laminating the support layer with an adhesive to the backing. The support layer can also be laminated to the adhesive 114 to attach the support layer 110 to the backing 112 as shown in FIGS. 1A-1C.

Other ways of permanently attaching the support layer 110 include irreversible heat bonding or ultrasonically welding of the support layer 110 to the backing 112. In at least one embodiment, the support layer 110 can be attached on the top of the backing 112, between the backing 112 and the adhesive 114, or attached to the adhesive 114.

The article 100 includes an adhesive 114 or adhesive 114. An aspect of the present disclosure is that the adhesive 114 works with the backing 112 to improve conformability of the resulting article, particularly with skin or skin prepped with a hydrophilic substance. In at least one embodiment, the adhesive 114 is a pressure sensitive adhesive (PSA).

The adhesive 114 includes a bioactive agent which comprises one or more of an anti-microbial, anti-viral, anti-bacterial or anti-fungal agent. In a further aspect, the anti-microbial, anti-viral, anti-bacterial or anti-fungal agent includes, but is not limited to, a bioactive agent described above. In yet a further aspect, the PSA comprises one or more of one or more of an anti-microbial, anti-viral, anti-bacterial or anti-fungal agent. In a further aspect, the PSA comprises an anti-microbial.

In at least one embodiment, the anti-microbial is a cationic antimicrobial. In at least one embodiment, the cationic antimicrobial is organic. For example, this can include chlorhexidine salts, quaternary ammonium salts, octenidine dihydrochloride (and other octenidine salts), or combinations thereof. Examples of chlorhexidine can include chlorhexidine gluconate, chlorhexidine digluconate (CHG), chlorhexidine acetate, or chlorhexidine dichloride. The preferred bioactive agent is CHG.

Examples of quaternary ammonium salts include benzalkonium chloride, benzethonium chloride, methylbenzethonium chloride, cetalkonium chloride, cetylpyridinium chloride, cetrimonium, cetrimide, dofanium chloride, tetraethylammonium bromide, didecyldimethylammonium chloride and domiphen bromide. In at least one embodiment, the cationic antimicrobial is non-organic, e.g., silver ion.

The bioactive agent can also be compositions of iodine, e.g., povidone-iodine.

In at least one embodiment, the bioactive agent is generally hydrophilic or has hydrophilic components. Generally, 0.5 wt. % to 10 wt. %, 1 wt. % to 10 wt. %, 2 wt. % to 10 wt. % of the bioactive agent can be present in the total adhesive composition. In some embodiments, 0.5 wt. % to 8 wt. %, or 0.5 wt. % to 5 wt. % of the bioactive agent can be present in the total weight of the adhesive 114.

In at least one embodiment, the article 100 comprises a bioactive agent wherein the bioactive agent impregnates one or both of the conformable backing 112 and/or the adhesive 114 coated onto the conformable backing 112. The adhesive 114 is disposed on a major surface of the backing 112. In at least one embodiment, the adhesive 114 is disposed only on one side of the backing 112.

The adhesive 114 can include a (meth)acrylic copolymer or copolymer comprising a crosslinked reaction product (includes partially crosslinked reaction products) of a curable composition or a non-crosslinked composition of a (meth)acrylic precursor that is an at least partially polymerized reaction product of a first monomer or a second monomer.

The (meth)acrylic precursor can be 70 to 90 wt. percent precursor, 75 to 85 wt. percent precursor, or even 75 to 80 wt. percent precursor to the total adhesive composition (e.g., the precursor, and plasticizers, bioactive agents, dyes, or other additives).

The (meth)acrylic precursor can include a first monomer. The first monomer can be from 75 to 95 wt. % (inclusive), 80 to 90 wt. % (inclusive), 81 to 89 wt. % (inclusive), 82 to 88 wt. % (inclusive), 83 to 87 wt. % (inclusive), or 84 to 86 wt. % (inclusive) of the (meth)acrylic precursor.

The first monomer can have a formula of $CH_2{=}C(R^1)-(CO)-OR^2$, where $R^1$ is hydrogen or a methyl group, and $R^2$ is an alkyl, heteroalkyl, alkenyl, or aryl group. In at least one embodiment, $R^2$ of the first monomer is an alkyl group having 1 to 14 carbon atoms, 1 to 12, or preferably 7 to 9 carbon atoms. $R^2$ of the first monomer can be a linear, branched, or aliphatic (such as a cycloaliphatic) alkyl group. Examples of the first monomer can include isooctyl acrylate, 2-ethylhexyl acrylate, lauryl acrylate, isobutyl acrylate monomers, or combinations thereof.

The (meth)acrylic precursor can include a second monomer. The second monomer can be from 5 to 25 wt. % (inclusive), 10 to 20 wt. % (inclusive), 11 to 19 wt. % (inclusive), 12 to 18 wt. % (inclusive), 13 to 17 wt. % (inclusive), or 14 to 16 wt. % (inclusive) of the (meth)acrylic precursor.

In at least one embodiment, the second monomer can be a vinyl monomer. The second monomer can be expressed by the formula $CHR^3{=}CH-R^4$. $R^3$ can be a hydrogen or a methyl group. In at least one embodiment, $R^4$ includes an acetate ester group (e.g., the second monomer is vinyl acetate). In at least one embodiment, $R^4$ includes an amide group. For example, if including an amide group, $R^4$ can also be expressed by $-C(O)-N(R^5)R^6$ where $R^5$ and $R^6$ are selected from hydrogen and linear or branched alkyl groups having a carbon number of 1 to 4. $R^5$ and $R^6$ are not both hydrogen at the same time.

In at least one embodiment, $R^4$ includes cyclic amide monomers. Specific examples of the second monomer having cyclic amide monomers include N-vinylcaprolactam (NVC), N-vinylpyrrolidone (NVP), and the like.

The adhesive 114 can also include a solubilizer. The solubilizer generally can increase the solubility of the bioactive agent in the adhesive composition. The solubilizer will depends on the bioactive agent. Solubilizers for CHG are discussed as a hydrophobic vehicle in U.S. Patent App. No. US 2016/0296678 and US2015/0238444A1 which are incorporated by reference in their entirety.

The solubilizer is generally hydrophobic and has a hydrophilic-lipophilic balance of no greater than 10. The solubilizer includes monoacylglycerides, alcohols (such as diols), and ether groups. Specific examples of monoacylglycerides include glycerol monocaprylate, glycerol monolaurate, glycerol monoisostearate, glycerol monooleate, decaglyceryl tristearate, dibutyl-L-tartrate, diethyl-L-tartrate, diethyl-D-tartrate, and combinations thereof. Specific examples of alcohols include 1,2-octane diol, 1,2-decane diol, 1,2-pentanediol, 1,2-propanediol, 1,2,6-trihydroxy-hexane, 1,3-propanediol, 1,4-butanediol, 2-butene-1,4-diol, 1,3-butanediol, 3-methyl-1,3-butanediol, 1,3-cyclohexanediol, 2,3-butanediol, and combinations thereof. Specific examples of ethers include triethylene glycol, tetraethylene glycol, triethyleneglycol monomethyl ether, diethyleneglycol monomethyl ether, diethyleneglycol monoethyl ether, Sorbeth-6, 1,3-dihydroxyacetone dimer, ethylhexyl glycerin, and combinations thereof.

In at least one embodiment, at least 3, 4, 5, 6, 10, 15, or 20 wt. % of the bioactive agent is solubilized in the solubilizer based on the combined weight of the bioactive agent and the solubilizer.

In at least one embodiment, at least 5 wt. %, at least 6 wt. %, at least 7 wt. %, at least 8 wt. %, at least 9 wt. %, or at least 10 wt. % of the bioactive agent is solubilized in the adhesive 114 based on the weight of the adhesive composition. In at least one embodiment, no greater than 20 wt. %, no greater than 10 wt. % of the bioactive agent is solubilized in the adhesive 114 based on the weight of the adhesive composition.

In at least one embodiment, the adhesive 114 does not have significant amount of a hydrophilic vehicle (exclusive of water) having an hydrophilic-lipophilic balance (HLB) above 10 such as alcohol, or glycerin. In some embodiments, the adhesive 114 contains little or no hydrophilic vehicle, i.e., vehicles having an HLB of greater than 10. As used herein, water is considered a separate component independent of any hydrophilic vehicles; therefore, the following amounts are exclusive of any water which may be present in the composition. In some embodiments, the compositions comprise no greater than 2 parts by weight hydrophilic vehicle per 1 part by weight bioactive agent, e.g., no greater than 1 part by weight, no greater than 0.5 part by weight, or even no greater than 0.1 part by weight hydrophilic vehicle per 1 part by weight bioactive agent.

In some embodiments, the adhesive 114 comprises no greater than 1 part by weight water per 1 part by weight bioactive agent, e.g., no greater than 0.5 part by weight, no greater than 0.1 part by weight, or even no greater than 0.01 part by weight water per 1 part by weight bioactive agent.

The adhesive 114 can also include a plasticizing agent that is added to the adhesive composition. The plasticizing agent is selected based on the hydrophobicity. In particular, the plasticizing agent makes the resulting adhesive 114 overall hydrophobic. In at least one embodiment, the plasticizing agent can have a weight average molecular weight of at least 1500, at least 1700, at least 1900, at least 2000, or at least 2500.

In at least one embodiment, the amount of plasticizing agent used depends upon the desired level of tack in the resultant activated adhesive 114 (i.e., the plasticized pressure sensitive adhesive), the level of peel and shear strength desired, the level of permanence desired, and the level of tackification of the latent, over-tackified, adhesive. For example, as the modulus of a latent, over-tackified, adhesive increases, higher levels of plasticizing agent are necessary to bring the adhesive modulus down into the useful range for pressure sensitive bond making (i.e., the shear storage modulus is below the Dahlquist criterion).

As the amount of plasticizing agent in the adhesive 114 is increased, maintaining cohesive strength becomes increasingly difficult, thus creating a practical upper limit on the amount of plasticizing agent that can be tolerated in the final adhesive 114. High levels of plasticizing agent may be beneficial if properties such as aggressive tack, low temperature performance, or smooth peel are required. Considering practical constraints for pressure sensitive adhesive formulation, it should be clear that there is also an upper limit for the shear modulus of the latent, over-tackified, adhesive to begin with and still enable pressure sensitive behavior with plasticizing agent loadings of 100 pph or less. Actual modulus values are difficult to define as it strongly depends on the type of plasticizing agent, plasticizing efficiency, and the compatibility of the plasticizing agent with the latent, over-tackified, adhesive.

In at least one embodiment, the plasticizing agent can be added such that the amount of plasticizing agent is within 3 wt. %, 2 wt. %, 1 wt. %, or at least equal to the amount of solubilizer added. In at least one embodiment, the amount of plasticizing agent can be at least 5 wt. %, at least 6 wt. %, at least 7 wt. %, at least 8 wt. %, at least 9 wt. %, or at least 10 wt. % of the total weight of the adhesive composition.

The plasticizing agent can be a polyol such as an oligomeric polyol including monomeric polyols, hydroy-terminated polyalkadienes, hydrogenated polyalkadiene polyols, and silicone polyols. In at least one embodiment, the plasticizing agent can be different from the polyol that may form the polyurethane linkages. For example, monomeric polyols, such as the $C_{36}$ dimer fatty alcohol available as PRIPOL 2033 from Unichema North America, Chicago, Ill., USA, can be used. Oligomeric polyols that have, on average, from about 1.6 to about 4 hydroxyl or amino groups can be used. One type of oligomeric polyol is aliphatic polyester polyol based on diacids and/or diols that have greater than 10 carbon atoms and preferably greater than 20 carbon atoms. Commercially available polyester polyols are PRIPLAST 3191, 3192, 3196, 3197, 1906, and 1907 from Unichema North America, Chicago, Ill., USA, which are believed to be based on 36 carbon atom diacids and/or diols. Specific constituents used in preparation of these diols are believed to be: for PRIPLAST 3192—dimer acid, adipic acid, and 1, 6-hexane diol; for PRIPLAST 3193—dimer acid and ethylene glycol; for PRIPLAST 3194—dimer acid, adipic acid, and ethylene glycol; for PRIPLAST 3196—dimer acid and 1,6-hexane diol; for PRIPLAST 3197—dimer acid and dimer diol; for PRIPLAST 1906—isophthalic acid and dimer diol; and for PRIPLAST 1907-terephthalic acid and dimer diol. The term "dimer acid" is understood to be a $C_{36}$ diacid formed by dimerization of unsaturated $C_{18}$ fatty acids and "dimer diol" is a $C_{36}$ difunctional polyol formed by hydrogenation of the $C_{36}$ dimer acid.

In at least one embodiment, the plasticizing agent can lower the latent, over-tackified, adhesive's $T_g$ to below about 10° C., preferably below 0° C., and its shear storage modulus to below the Dahlquist criterion, which is defined in the *Handbook of Pressure Sensitive Adhesive Technology*, Donatas Satas (Ed.), $2^{nd}$ Edition, pp. 172-173, Van Nostrand Reinhold, New York, NY, 1989.

In at least one embodiment, the conformable backing 112 can be a gauze, a sheet material with absorbent properties, a patch or the like wherein the conformable backing 112 is impregnated with a bioactive agent. In at least one embodiment, the adhesive 114 is hydrophobic and the bioactive agent, such as a cationic antimicrobial such as CHG, is solubilized in the adhesive 114.

The adhesive 114 can form a substantially uniform layer on the backing 112 sufficient to impart adhesive properties to the backing 112. The adhesive 114 can be reasonably skin compatible and "hypoallergenic," such as the acrylate copolymers described in U.S. Pat. No. RE 24,906.

In at least one embodiment, the adhesive-coated backing 113 (i.e., the combination of both the adhesive 114 and the backing 112) transmits moisture vapor at a rate of at least 300 $g/m^2$/24 hrs/37° C./100-10% RH, frequently at least 700 $g/m^2$/24 hrs/37° C./100-10% RH, and most typically at least 2000 $g/m^2$/24 hrs/37° C./100-10% RH using the inverted cup method as described in U.S. Pat. No. 4,595,001. Further, suitable surface treatments on the backing 112 and optional tie layers can be used to improve the interfacial bonding between the backing 112 and the adhesive 114, such as corona treatment, plasma treatment, chemical treatment etc.

The article 100 can also have a release liner 116 disposed on a portion of the adhesive 114. release liner 116 films suitable for use with embodiments of the present disclosure can be made of kraft papers, polyethylene, polypropylene, polyester or composites of any of these materials. The films are preferably coated with release agents such as fluorochemicals or silicones. For example, U.S. Pat. No. 4,472,480 describes low surface energy perfluorochemical liners. The liners are papers, polyolefin films, or polyester films coated with silicone release materials. Examples of commercially available silicone coated release papers are POLYSLIK™, silicone release papers available from Rexam Release (Bedford Park, Ill.) and silicone release papers supplied by Loparex Group (Willowbrook, Ill.).

As shown in FIG. 1B, the release liner 116 is removable from the adhesive 114 and peels off so that the adhesive 114 can be placed on a surface such as a topographical surface (e.g., intact or punctured human skin, with or without an antiseptic solution).

As shown in FIG. 1C, the article 100 can have grip portions (not shown) that are adjacent to the first side edge 101 and second side edges 102 of the article 100. The grip portions can function as gripping points for a user to apply the article 100 onto a patient. In at least one embodiment, the user can be a clinician such as doctor or a nurse, a robotic assistant, or the patient his or herself.

The side edges 101, 102, and top and bottom edges 103, 104 can form at least part of a perimeter 106 of the article 100. Further, the article 100 is shown having a top surface 105 where an optional carrier 110 forms a frame along the perimeter 106.

Figures 2A, 2B, 2C:
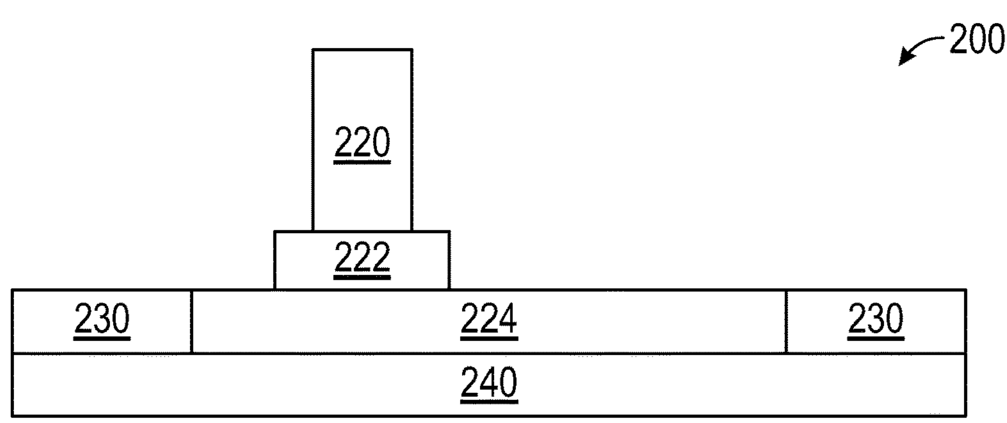
FIGS. 2A-2C illustrate the article of FIGS. 1A-1C disposed on the topographical surface, according to an aspect of the present disclosure.

FIGS. 2A-2C illustrate a system 200 that includes a topographical surface 240. The topographical surface 240 can be an anatomical surface and more specifically a dry human skin site or flat area such as the abdominal area of the patient. As described herein, FIGS. 2A-2C can illustrate the concepts at method 300 in FIG. 3.

In FIG. 2A, a surgical article 230, such as a drape, can be placed on the topographical surface 240. The surgical article 230 can be a nonwoven or a plastic film as commonly used. In at least one embodiment, the surgical article 230 is part of an incise drape commercially available under the trade designation Steri-Drape sold by 3M.

An applicator 220 can be used to provide an antiseptic solution 224 having a bioactive agent to the topographical surface 240. The applicator 220 can include an application surface 222 (e.g., a sponge-like member) which can distribute the antiseptic solution 224 and a reservoir 221 that contains the antiseptic solution 224.

In at least one embodiment, the antiseptic solution 224 can include an alcohol carrier which may also function as the primary antiseptic. The antiseptic solution 224 can include a polymer to stabilize the antiseptic solution 224 or the bioactive agent. The antiseptic solution 224 can also be film-forming meaning that it forms a film of residue after the alcohol carrier has evaporated. The film-forming compositions are commercially available under the trade designation ChloraPrep by BD (Franklin Lakes, NJ) or DuraPrep by 3M (Saint Paul, MN).

In FIG. 2B, a user can apply the antiseptic solution 224 to the topographical surface 240. This can correspond to block 320 in FIG. 3, where the antiseptic solution 224 is applied to at least a portion of the topographical surface 240. The antiseptic solution 224 may be applied in a non-continuous layer. The user can allow the antiseptic solution 224 to dry. For example, after a period of time, some of the alcohol carrier may evaporate, leaving behind a film on the topographical surface. Both the film and the alcohol carrier can interfere with adhesion of the article 100 and cause lifting. An aspect of the present disclosure is that the article will not substantially lift from the topographical surface 240 after the antiseptic solution 224 is applied.

Figure 3:
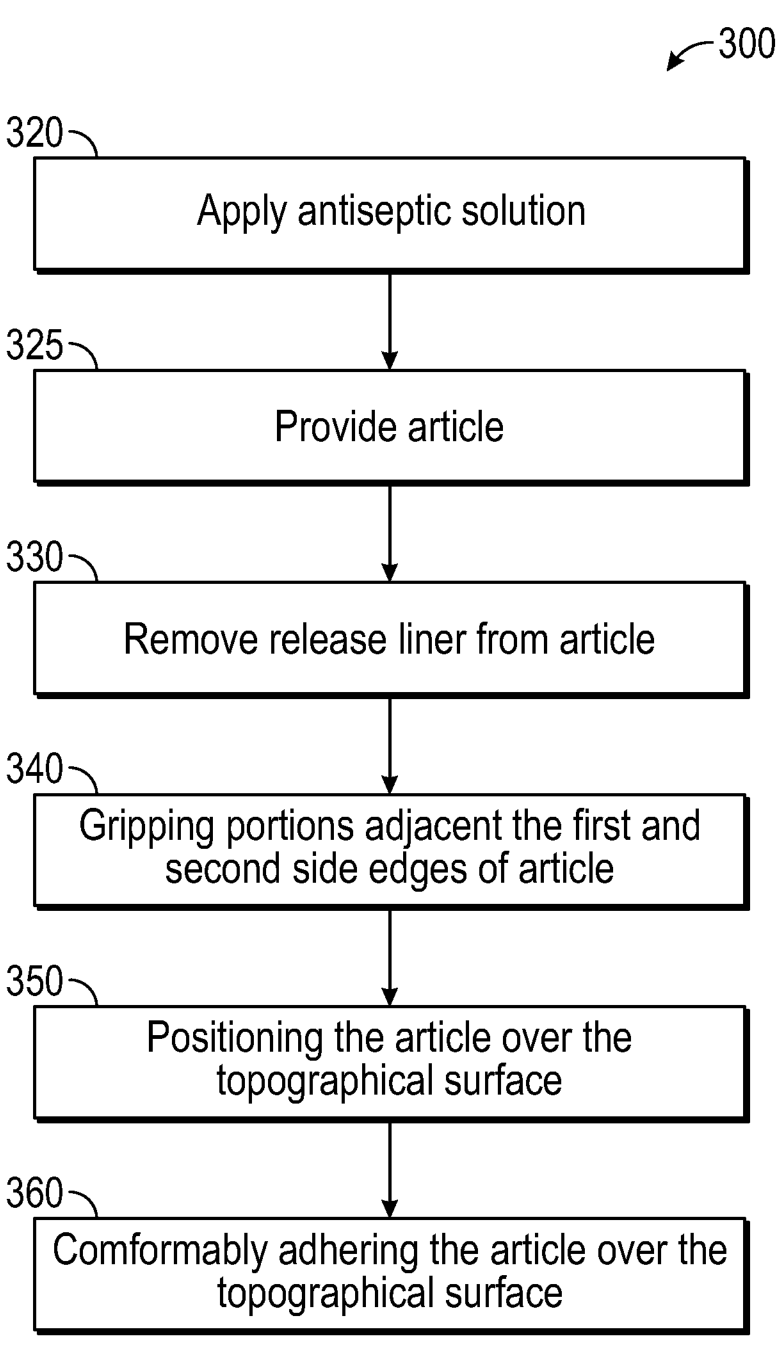
FIG. 3 illustrates a flowchart of a method of applying the article, according to an aspect of the present disclosure.

In FIG. 2C, a user obtains the article 100 in FIG. 1 which is described in block 425 in FIG. 3. As shown, the user can also optionally remove the release liner 116 from the adhesive 114 as described in FIG. 1C and block 330 in FIG. 3.

In block 340 in FIG. 3, the user can further grip portions that are adjacent to first and second side edges of the article 100 (as shown in FIG. 1C).

In block 350 in FIG. 3, the user can position the article over the topographical surface 240 and use force to apply the article 100 toward the topographical surface 240.

In block 360, the article 100 can be placed over both the topographical surface 240 and at least part of the antiseptic solution 224 or the residue left by the antiseptic solution 224. Article 100 may also adhere to the surgical article 230 and substantially conform to the surgical article 230, the antiseptic solution 224, and the topographical surface 240.

Figure 4:
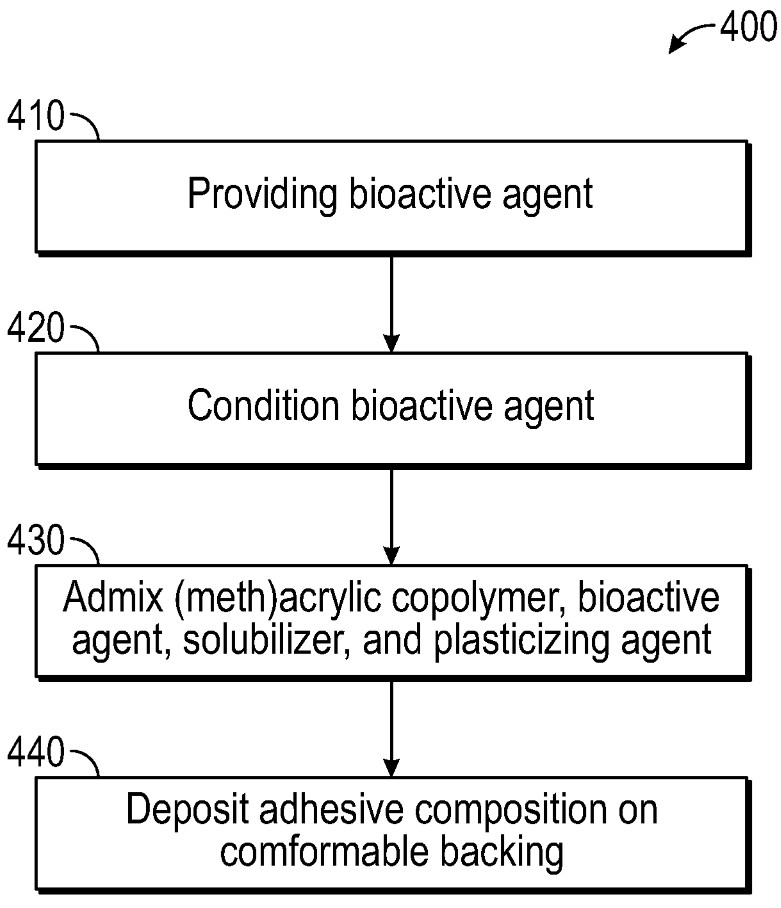
FIG. 4 illustrates a flowchart of a method of making the article, according to an aspect of the present disclosure.

FIG. 4 illustrates a flowchart of a method 400 for preparing the article 100 in FIG. 1. The method 400 can begin in block 410 where a bioactive agent is provided. Some bioactive agents useful in the present disclosure can be provided in aqueous solutions. For example, commercially available CHG can be found in concentrations of up to 20 wt. % in water.

In block 420, the bioactive agent can optionally be conditioned. In at least some embodiments, water can be removed from the bioactive agent to ease handling. For example, there can be at least three distinct methods for preparing solutions of CHG in a non-aqueous vehicle. The first method involves mixing an aqueous CHG solution with a relatively high boiling vehicle, and then pulling a vacuum on the mixture to remove the water (the "Vacuum Method"). The second method involves lyophilizing CHG, and then dissolving the CHG into the vehicle (the "Lyophilizing Method"). The third method involves generating the CHG in situ by reacting gluconolactone, a limited amount of water, and chlorhexidine free base (the "In Situ Method").

In block 430, the (meth)acrylic copolymer can be admixed with the bioactive agent, the solubilizer and plasticizing agent to form the adhesive composition. In at least one embodiment, the (meth)acrylic copolymer can also be combined with a solvent. The (meth)acrylic copolymer can also be admixed with the bioactive agent at room temperature or above, including elevated temperatures.

In block 440, the adhesive composition can be deposited on the backing. In at least one embodiment, a solvent can be added in block 430 or block 440 to aid in processing. The deposition in block 440 can also be performed without the aid of a solvent (e.g., hot melt adhesive techniques as described in U.S. Pat. No. 4,049,483).

EXAMPLES

Objects and advantages of various embodiments of the present disclosure are further illustrated by the following examples, but the particular materials and amounts thereof recited in these examples, as well as other conditions and details, should not be construed to unduly limit the various embodiments of the present disclosure. Unless otherwise indicated, all parts and percentages are on a weight basis, all water is distilled water, and all molecular weights are weight average molecular weight. Compositions are reported as weight percentages (wt %) unless noted otherwise.

Test Methods

Tensile and Elongation

A Zwick Universal Tabletop Tensile Tester, Model Z005 (Zwick USA, Kennesaw, GA) was used to measure the tensile properties based on ASTM D882 and ASTM D3759. Test sample size: 1 inch (2.54 cm) wide by 5 inches (12.7 cm) long. Gauge length: 1 inch (2.54 cm) with crosshead speed of 10 inches (25.4 cm)/min. Test specimens were squarely tabbed crosswise at each end with a 1 inch (2.54 cm) wide piece of tabbing tape overlapped once in such a way as to leave only the specified gauge length exposed and leave the ends of the tape tabs outside of the jaw faces. The force required to elongate the test specimen to 25% strain (Fx25) was used to represent the backing or drape conformability.

Bonding Strength of Pressure Sensitive Adhesive to Backing Material

The Zwick Tensile Tester was used to measure the force necessary to remove a pressure sensitive adhesive from its backing using anodized aluminum panels as the test surface, with backing tape 3M #2525 tape and, if required, 3M #2262 adhesive for reinforcement of the film (both available from 3M Company, St. Paul, MN). Sample size: ½ inch (1.27 cm) wide by 4 inches (10.16 cm) long. Gauge length: 10 inches (25.4 cm) with crosshead speed of 200 mm per minute.

Knee Flexion Model Study

A knee flexion model was used to evaluate the drape adhesion to skin and drape removal performance of the chlorhexidiene digluconate (CHG) antimicrobial incise drapes. The knee flexion model was used to simulate surgical conditions.

Figure 5:
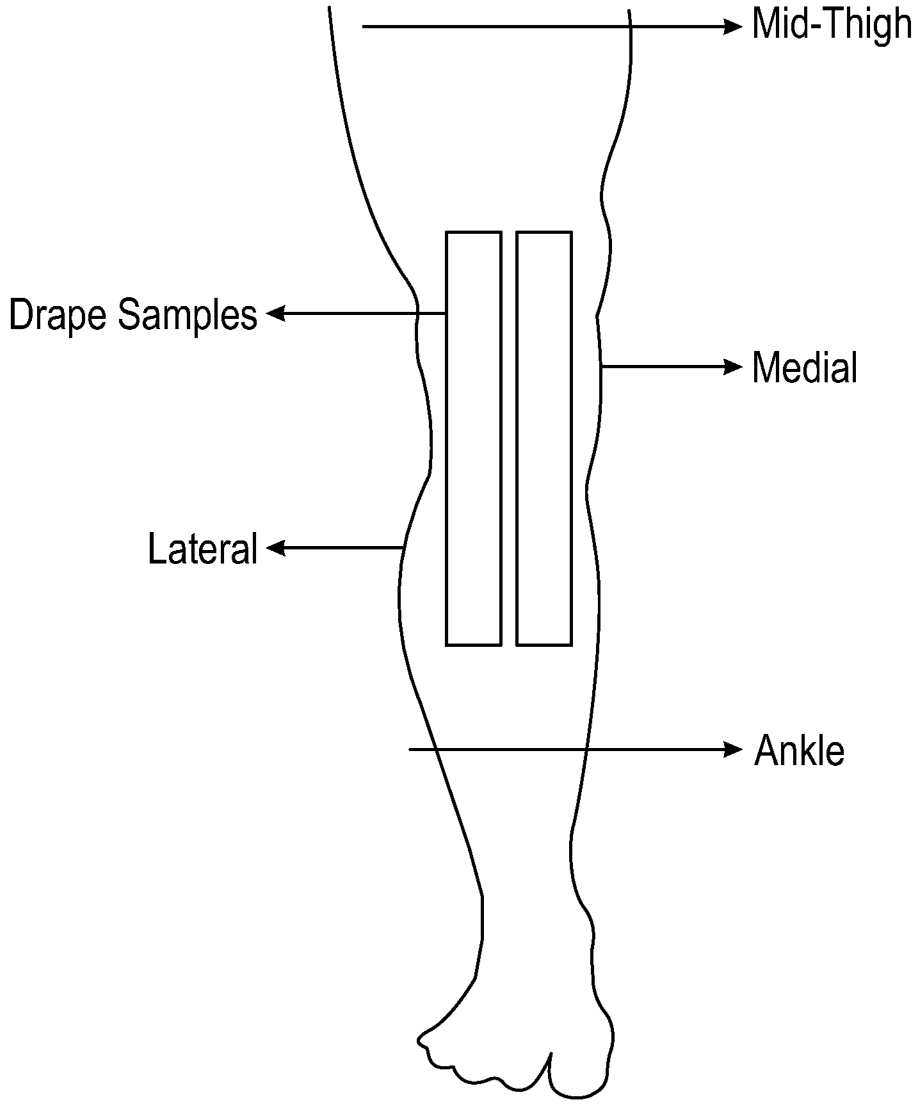
FIG. 5 is an illustration of a Knee Model Flexion Study described herein, according to an aspect of the present disclosure.

In the study, the test subject was sitting or lying on a padded examination table. If an excessive amount of hair existed on the test sites, the areas were clipped prior to the initiation of the study to ensure good sample-skin contact. Both legs were prepped with the desired surgical prep, such as ChloraPrep Hi-Lite Orange® (ChloraPrep, Becton-Dickinson, Franklin Lakes, NJ) or DuraPrep Surgical Solution (DuraPrep, 3M Company, St. Paul, MN). After at least 3 minutes air drying of the skin preparation, the legs were draped. Each subject had two 3 inch (7.62 cm)×10 inch (25.4 cm) (area of 30 square inches or 19354.8 $mm^2$) drape samples applied to each leg longitudinally over the knee to the left and right side of the midline. An approximate ¼ inch (0.635 cm)-½ inch (1.27 cm) gap was left between the two drapes from about 3 inches (7.62 cm) above the knee cap (i.e., upper edge of the knee cap) to 3 inches (7.62 cm) below the knee, as shown in FIG. 5.

Figure 6:
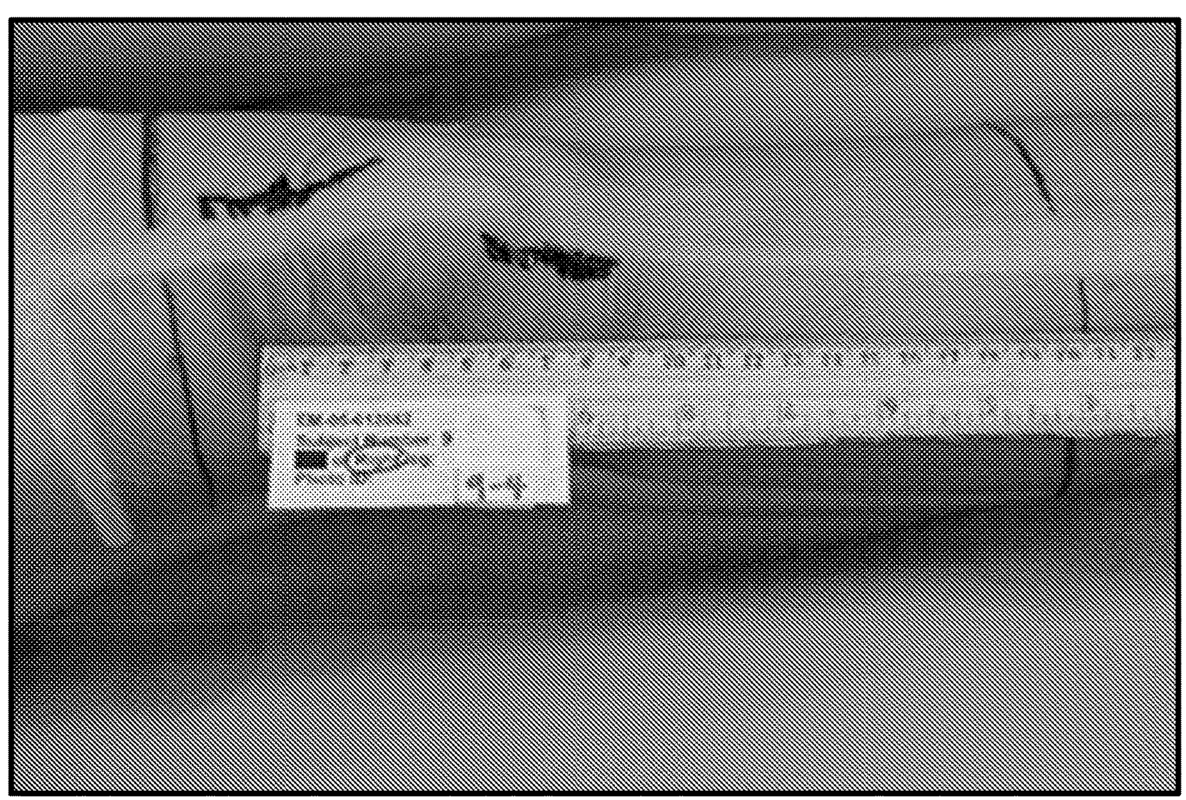
FIG. 6 is a photograph of a knee with the article used in the Knee Model Flexion Study described herein, according to an aspect of the present disclosure.

Drape samples were worn for approximately ½ hour. Drape lift was evaluated after a dry flex challenge (flexing the knees 10 times as far as comfortable and extending straight), a wet flex challenge (applying saline-soaked gauze to cover the midline for 5 minutes followed by 10 knee flexes), and after a pulse lavage challenge (applying 200-300 cc saline solution along the midline between the two drapes using low setting pulse lavage). Areas of drape lift were marked and photographed after each challenge, as shown in FIG. 6. At the end of the pulse lavage lift assessment, the drape samples and excess skin prep were removed. Assessments of skin condition (irritation and stripping), adhesive residue, ease of removal, and subject's assessment of pain level were performed after drape removal. Geometric mean of lifted area ($mm^2$) and frequency of lift (%) were reported for all test subjects of each clinical study.

Full Drape Removal Study

A full drape removal study was conducted to evaluate the drape handling and removal performance using a full-sized drape on the legs of healthy subjects. The test subject was sitting or lying on a padded examination table. If an excessive amount of hair existed on the test sites, the areas were clipped prior to the initiation of the study to ensure good sample-skin contact. Subjects were required to remain in the study room during the 1-hour wear-time.

Both legs were prepped with DuraPrep™ Surgical Solution by 3M (St. Paul, MN) ("DuraPrep"). After at least 3 minutes air drying of the skin preparation, the legs were draped with 10 inch (25.4 cm)×13 inch (33.02 cm) test samples. Drape samples were worn for approximately 1 hour. The subject flexed both knees fully 10 times every 10 minutes during the hour. Six sets of knee flexes (60 flexes total) were performed. At the end of the wear-time, the drape samples and excess skin prep were removed. Assessments for ease of drape application, ease of drape removal, and discomfort when drape was removed were performed.

Preparative Examples

TABLE 1

Materials for antimicrobial adhesive.

| Materials | Source | Function |
|---|---|---|
| Pressure Sensitive Adhesive (PSA) (85 wt % isooctyl acrylate (IOA) and 15 wt % N-vinyl pyrrolidone (NVP)) | 3M (St. Paul, MN) | Adhesive |
| Chlorhexidine Digluconate (CHG) 20 % w/v solution in water | Medichem SA (Spain) | Bioactive Agent |
| Glycerol monoisostearate (GMIS) | Croda International plc (UK) | Solubilizer |
| PRIPLAST 3197 | Croda International plc (UK) | Plasticizing Agent |
| FD&C red #40 | Sensient Technologies (Milwaukee, WI) | Dye |

Preparation of an Antimicrobial Adhesive Composition

The chlorhexidine digluconate (CHG) antiseptic agent was solubilized in a hydrophobic vehicle as described in U.S. Pat. No. 9,713,659.

An antimicrobial adhesive solution was prepared by blending together using simple manual agitation a solution of the pressure sensitive adhesive [25% PSA in solvent] and the CHG in hydrophobic vehicle with the GMIS, PRIPLAST 3197, and the dye in solvent to produce a CHG-containing antimicrobial adhesive solution comprising 78.48 wt % PSA, 2 wt % CHG, 10 wt % GMIS, and 9.75 wt % Priplast 3197, and 0.02 wt % FD&C red #40 dye.

TABLE 2

Polymers.

| Brand | Polymer chemistry | Supplier | Shore A Hardness |
|---|---|---|---|
| HYTREL 4056 | thermoplastic polyester elastomer | DuPont Company | 90 |
| ESTANE 58309 | polyether-based polyurethane elastomer | Lubrizol Advanced Materials, Inc. | 85 ± 3 |
| ESTANE 58300 (EZ14-10-A) | aromatic polyether-based polyurethane elastomer | Lubrizol Advanced Materials, Inc. | 82 |
| ELASTOLLAN ET870 | aromatic polyether-based polyurethane elastomer | BASF Corporation | 73 ± 3 |
| TEXIN 1209 (TEXIN RxT70A) | aromatic polyether-based polyurethane elastomer | Bayer MaterialScience LLC | 70 |
| ESTANE 58280 | aromatic polyether-based polyurethane elastomer | Lubrizol Advanced Materials, Inc. | 79 |

TABLE 2-continued

| Polymers. | | | |
|---|---|---|---|
| Brand | Polymer chemistry | Supplier | Shore A Hardness |
| ESTANE 58123 | aromatic polyether-based polyurethane elastomer | Lubrizol Advanced Materials, Inc. Lubrizol Advanced | 70 |

Extrusion of Polymer Films

Polymer films used as backing materials were extruded using a Haake single screw extruder (Bench 300) from Thermo Fisher Scientific Inc. (Germany) on a paper liner according to the extrusion conditions in Table 3.

TABLE 3

| Extrusion conditions. | | | | | |
|---|---|---|---|---|---|
| Material | Thickness (thousandths of an inch, mil) | Zone 1 | Zone 2 | Zone 3 | Die Zone set point |
| Texin 1209 | 1 | 320° F. | 340° F. | 360° F. | 360° F. |
| Estane 58123 | 1 | 320° F. | 340° F. | 360° F. | 360° F. |
| Elastollan ET870 | 0.8 | 320° F. | 340° F. | 360° F. | 375° F. |
| Estane 58300 | 0.8 | 320° F. | 340° F. | 360° F. | 360° F. |
| Estane 58309 | 0.8 | 320° F. | 340° F. | 360° F. | 375° F. |
| Hytrel 4056 | 0.8 | 320° F. | 340° F. | 360° F. | 360° F. |

Figure 7:
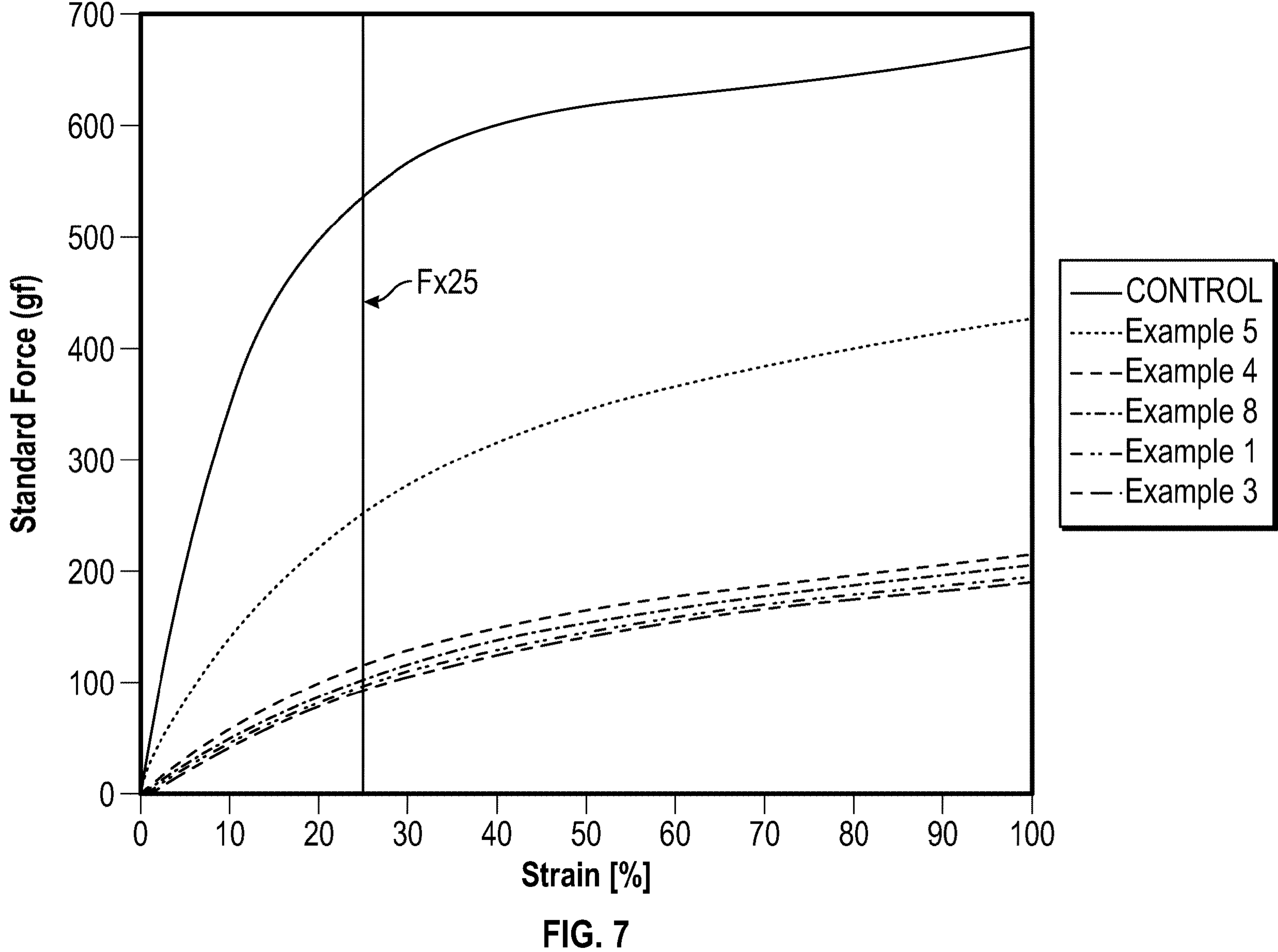
FIG. 7 is a graph of representative tensile & elongation curve of film backings, according to an aspect of the present disclosure.
Figure 8A:
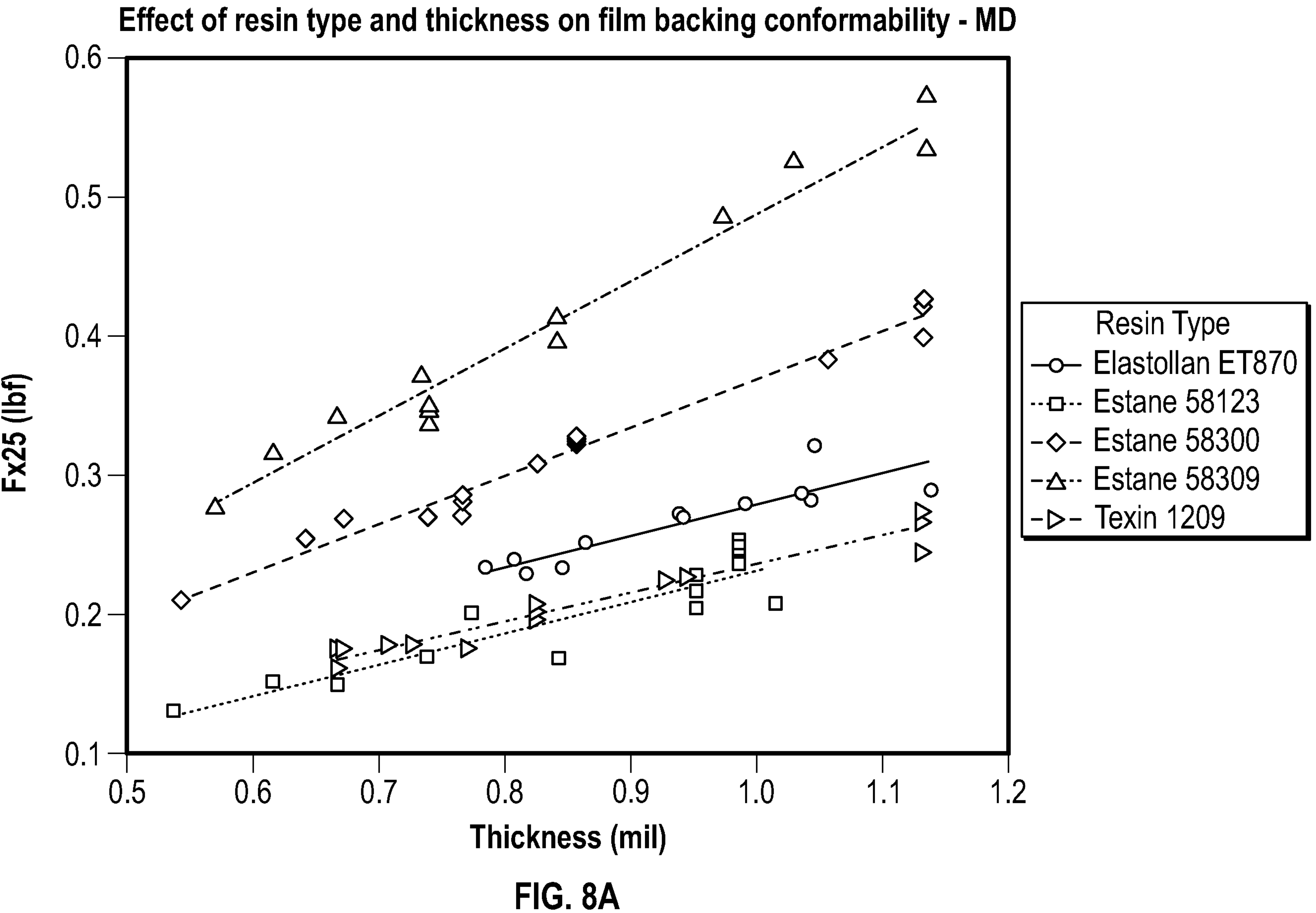
FIG. 8A illustrates a graph of the effect of resin type and thickness on film backing conformability in the machine direction, according to an aspect of the present disclosure.
Figure 8B:
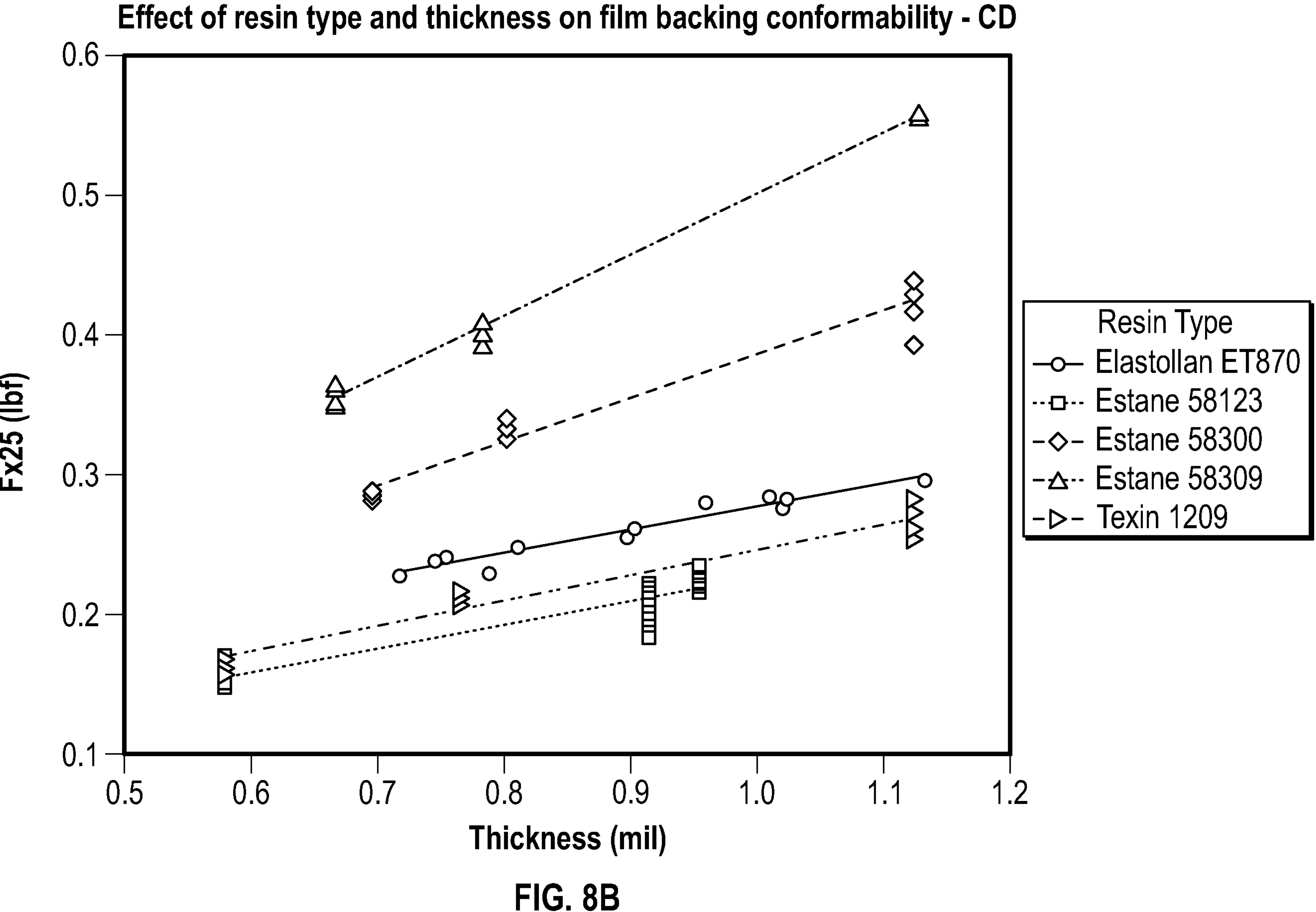
FIG. 8B illustrates a graph of the effect of resin type and thickness on film backing conformability in the cross direction, according to an aspect of the present disclosure.
Figure 9A:
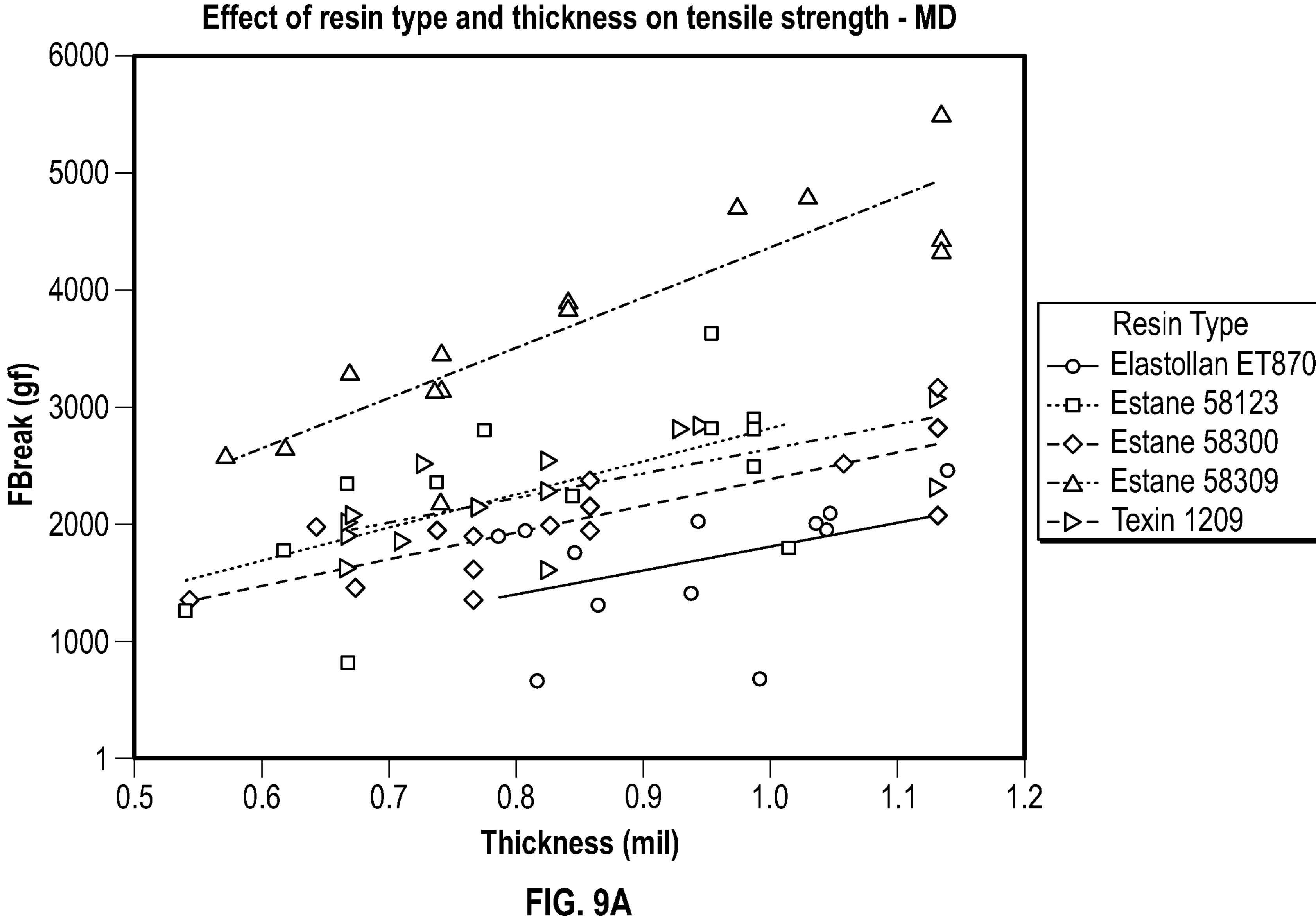
FIG. 9A illustrates a graph of the effect of resin type and thickness on film backing tensile strength in the machine direction, according to an aspect of the present disclosure.
Figure 9B:
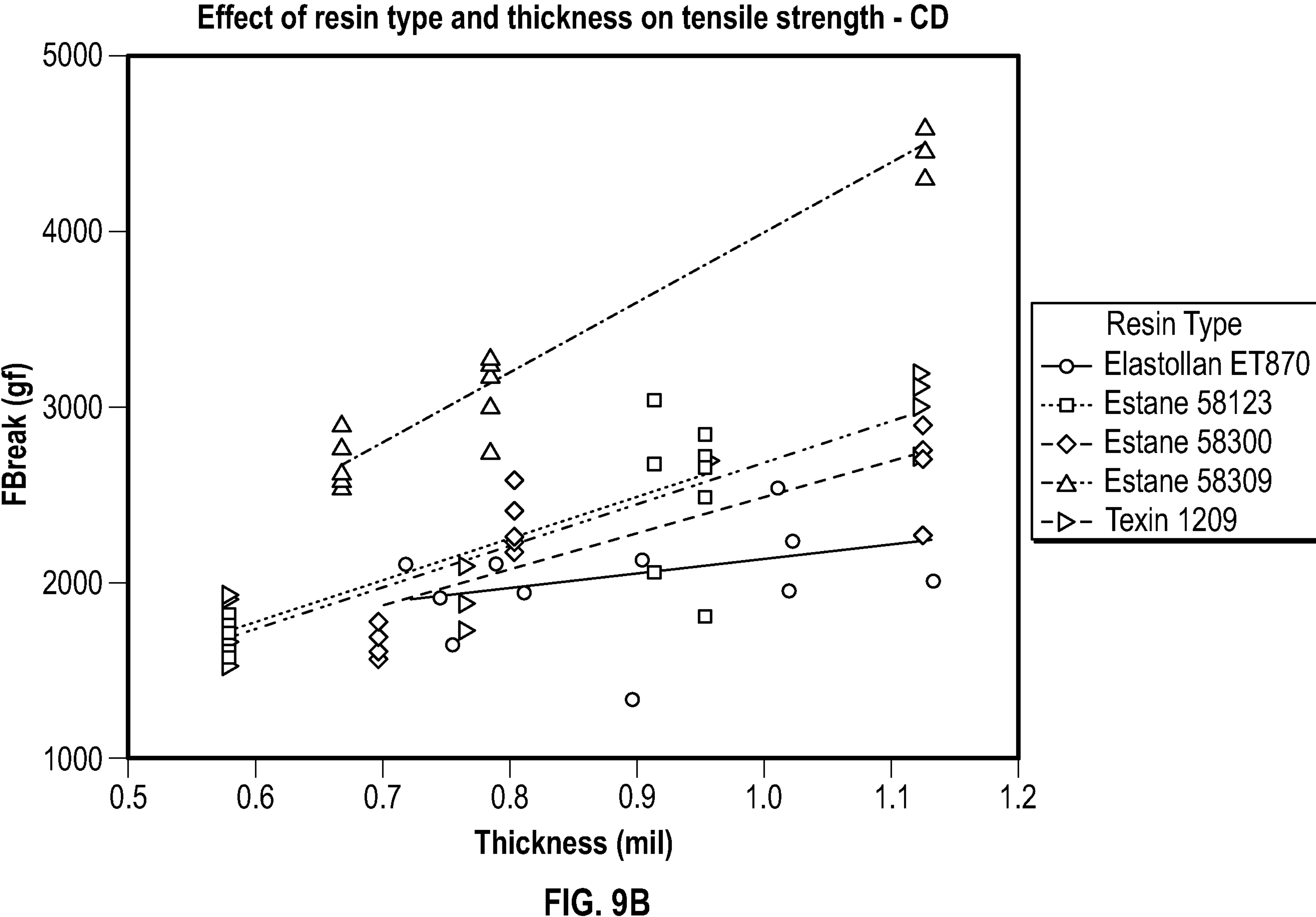
FIG. 9B illustrates a graph of the effect of resin type and thickness on film backing tensile strength in the cross direction, according to an aspect of the present disclosure.

The tensile and elongation properties of the film backings were tested as described in the Tensile and Elongation Test Method. The force required to elongate the test specimen 25% (Fx25) was identified to best represent the conformability of the film backings. Representative tensile & elongation curves are shown in FIG. 7. FIGS. 8A-8B show the effect of polymeric chemistry (resin type) and thickness on the conformability of the film backings for machine direction (MD) and cross machine direction (CD). Tensile strength (UTS, maximum force to break the test specimen) of the film backings in the machine and cross machine directions was also recorded and results are presented in FIGS. 9A-9B.

Lower Fx25 is preferred for better conformability. The order of conformability of the film backings from high to low is Estane 58123/Texin 1209, Elastollan ET870, Estane 58300, and Estane 58309 under similar film thickness. Lower film thickness also provides better conformability. However, lower film thickness results in lower tensile strength. Films made from Estane 58309 have higher tensile strength compared with films made from other resins of similar film thickness.

Preparation of Adhesive Coated Polymer Films

Portions of the antimicrobial adhesive composition prepared above were coated as hand-spreads by applying a uniform layer of the adhesive on the release surface of a siliconized release liner using a knife-edge coater. The wet adhesive coated thickness ranged from 50 to 510 micrometers (2-20 mils). The coated adhesives were dried in an oven for 1-10 minutes at temperatures between 65° C. and 93° C. (150° F. to 200° F.). The dried adhesives were laminated to the previously prepared extruded film backings using nip rollers at room temperature. Some samples of polymer films were surface treated prior to application of the adhesive solution, using either an air corona or $N_2$ corona. The polymer types and thicknesses, surface treatments, and adhesive coating weights are provided in Table 4.

Bonding strength of the antimicrobial pressure sensitive adhesive to the backings was evaluated using the method described in the Test Method section and the resulting values are provided in Table 4. Higher bonding strength is preferred to ensure no residual adhesive is left on the patient's skin during use, preferably, greater than 600 grams, more preferably greater than 800 grams. In Table 4, "Sterile" refers to whether the samples were sterilized prior to testing, and EO is sterilization using ethylene oxide.

TABLE 4

| Bonding strength of pressure sensitive adhesive to backings. | | | | | |
|---|---|---|---|---|---|
| Thermoplastic polymeric backing | | | Adhesive coating weight | Average bonding strength | |
| Polymer type | Thickness (mil) | Surface Treatment | (grains/24 in$^2$) | (grams/0.5 in) | Sterile |
| Texin Rx70A | 1.0 | None | 9 | 588 | None |
| Texin Rx70A | 1.0 | Air corona | 9 | 780 | None |
| Texin Rx70A | 1.0 | $N_2$ corona | 9 | 934 | None |
| Texin Rx70A | 1.0 | $N_2$ corona | 9 | 773 | EO |
| Estane 58123 | 1.0 | None | 9 | 502 | None |
| Estane 58123 | 1.0 | Air corona | 9 | 758 | None |
| Estane 58123 | 1.0 | $N_2$ corona | 9 | 805 | None |
| Estane 58123 | 1.0 | $N_2$ corona | 9 | 791 | EO |
| Estane 58300 | 0.8 | None | 9 | 800 | None |
| Estane 58300 | 0.8 | $N_2$ corona | 9 | 996 | None |
| Estane 58300 | 0.8 | $N_2$ corona | 9 | 916 | EO |
| Elastollan ET870 | 1.2 | None | 9 | 964 | None |
| Elastollan ET870 | 1.0 | None | 9 | 870 | None |
| Elastollan ET870 | 1.0 | None | 9 | 1062 | EO |
| Estane 58309 | 0.8 | None | 9 | 1166 | EO |

Examples 1-10

Selected extruded polymer films were coated with the antimicrobial pressure sensitive adhesive formulation described above at the target coating weight using the coating procedure described above. Table 5 provides details of the Examples. These Examples were then converted to the desired test sample size and EO sterilized for use in the knee flexion model study, which was conducted as described above. Additional samples were prepared for Fx25 measurement.

TABLE 5

| Description of examples 1-10. | | | | |
|---|---|---|---|---|
| | Thermoplastic polymeric backing | | | Adhesive |
| | Polymer type | Thickness (mil) | Surface Treatment | coating weight (grains/24 in$^2$) |
| Example 1 | Texin Rx70A | 1.0 | N2 corona | 9 |
| Example 2 | Elastollan ET870 | 1.0 | no | 9 |
| Example 3 | Estane 58123 | 1.0 | N2 corona | 9 |
| Example 4 | Estane 58300 | 0.8 | N2 corona | 9 |
| Example 5 | Estane 58309 | 0.8 | No | 9 |
| Example 6 | Estane 58309 | 0.8 | No | 9 |
| Example 7 | Estane 58309 | 0.8 | No | 9 |
| Example 8 | Elastollan ET870 | 0.8 | No | 9 |
| Example 9 | Elastollan ET870 | 0.7 | No | 9 |
| Example 10 | Elastollan ET870 | 0.9 | No | 9 |

Figure 10:
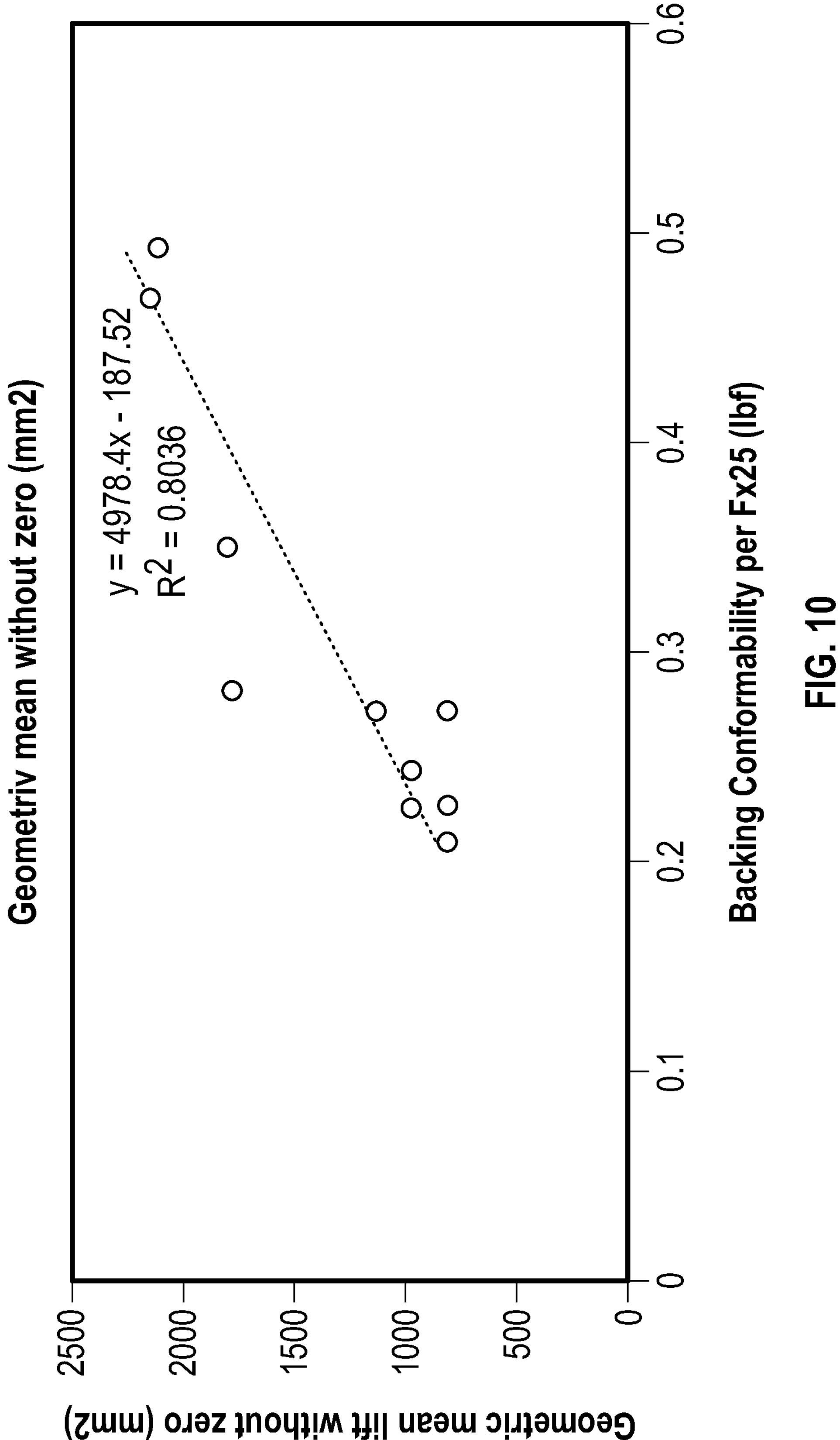
FIG. 10 illustrates a graph showing geometric mean of lift vs backing conformability in different studies, according to an aspect of the present disclosure.

The results of backing conformability tests and knee flexion model studies are shown in Table 6 and FIG. 10.

Lower lift areas (geometric mean of the non-zero values) were observed for the incise drapes made using more conformable backing films.

TABLE 6

Backing conformability and area of lift per knee flexion model studies.

| | Backing conformability Fx25 (lb$_f$/in) (g$_f$/cm) | Geometric mean of the non-zero values (mm$^2$)/ (as a percentage of drape area) | frequency of drape lift |
|---|---|---|---|
| Example 1 | 0.2262 (40.39) | 970/(5.0%) | 80% |
| Example 2 | 0.2726 (48.68) | 1130/(5.8%) | 67% |
| Example 3 | 0.2099 (37.48) | 800/(4.1%) | 83% |
| Example 4 | 0.282 (50.4) | 1770/(9.1%) | 83% |
| Example 5 | 0.4938 (88.18) | 2113/(10.9%) | 69% |
| Example 6 | 0.3505 (62.59) | 1800/(9.3%) | 95% |
| Example 7 | 0.469 (83.8) | 2150/(11.1%) | 60% |
| Example 8 | 0.2445 (43.66) | 970/(5.0%) | 57% |
| Example 9 | 0.2275 (40.63) | 800/(4.1%) | 64% |
| Example 10 | 0.2728 (48.72) | 800/(4.1%) | 75% |

Examples 11-15

Selected extruded films were coated with the pressure sensitive adhesive formulation described earlier at the target coating weight per the coating procedure described above. The coated samples were then converted to the desired test sample size and EO sterilized for the full drape removal study. Table 7 provides the details of these Examples. A commercially available IOBAN 2 Incise drape 6650 EZ was selected as the control.

TABLE 7

Description of Examples 11-15.

| | Thermoplastic polymeric backing | | Adhesive coating weight |
|---|---|---|---|
| | Polymer type | Thickness (mil) | (grains/24 in$^2$) |
| Example 11 | Elastollan ET870 | 1.2 | 9 |
| Example 12 | Elastollan ET870 | 1.0 | 6 |
| Example 13 | EZ14-10-A | 1.0 | 9 |
| Example 14 | EZ14-10-A | 0.8 | 9 |
| Example 15 | EZ14-10-A | 0.8 | 6 |

The handling performance and drape removal study was conducted on the legs of healthy subjects to compare the Examples 11-15 with the control (IOBAN 2 incise drape, 6650 EZ, available from 3M Company, St. Paul, MN). Ease of drape application, ease of drape removal, comfort/discomfort rating, and tearing performance were evaluated and are reported in Table 8.

TABLE 8

Results of full drape removal study.

| | Tearing | Ease of application | Comfort | Removal force |
|---|---|---|---|---|
| Example 11 | More than control | Similar to control | Similar to control | Similar to control |
| Example 12 | Similar to control | Similar to control | Similar to control | Similar to control |
| Example 13 | More than control | Similar to control | Similar to control | Similar to control |
| Example 14 | More than control | Similar to control | Similar to control | Similar to control |
| Example 15 | Similar to control | Similar to control | Similar to control | Similar to control |

Coated samples were also converted to the desired test sample size and EO sterilized for the knee flexion model study using the procedure described above. The control specimen (Hytrel 4056) was 1.0 mil in thickness with 9 grains/24 in$^2$ adhesive coating. The results of knee flexion model studies of selected Examples are shown in Table 9. Lower lift areas (geometric mean of the non-zero values) were observed for the incise drapes made using more conformable backing films.

TABLE 9

Backing conformability and area of lift per knee model studies.

| | Geometric mean of the non-zero values (mm$^2$) | Drape lift |
|---|---|---|
| Example 12 | 350 | 70% |
| Example 15 | 590 | 70% |
| Control (Hytrel) | 2611 | 100% |

Definitions

Throughout this specification, unless the context requires otherwise, the word "comprise," or variations such as "comprises" or "comprising," will be understood to imply the inclusion of a stated integer or step or group of integers or steps but not the exclusion of any other integer or step or group of integers or steps.

Singular forms "a," "an" and "the" include plural referents unless the context clearly dictates otherwise. Thus, for example, reference to "a bioactive agent" includes mixtures of two or more such agents, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Bioactive agent" refers to includes its equivalents, "drugs," and "medicament" and is intended to have the broadest meaning as including substances intended for use in the diagnosis, cure, mitigation, treatment or prevention of disease, or to affect the structure or function of the body. The bioactive agent, or an acceptable salt thereof, will be present in an amount such that the composition delivers a therapeutically effective amount for the indication being treated such as disinfection of the normal skin flora of a patient's skin.

"Conformable" or "conformability" refers to material that is conformable to a surface, including, but not limited to, anatomical surfaces. As such, when the backing is applied to a surface, it conforms to the surface. In some applications, the material chosen conforms even when the surface is moved and stretches to accommodate the movement, but is resilient enough to continue to conform to the surface when the surface is returned to its unmoved condition. Suitable materials include, for example, nonwoven fibrous webs, woven fibrous webs, knits, films, sheets, tapes, and other familiar backing materials. Such materials can be fabricated from both natural and man-made materials, including polymeric materials. Such conformable materials are conformable at least at temperatures from 35-45 degrees Celsius. With respect to the conformable synthetic film backings, the film should have a tensile modulus of less than about 400,000 psi as measured in accordance with ASTM D-638 and D-882, preferably less than about 300,000 psi.

"Dry human skin site" refers to the knee or elbow of a person.

"Film-forming" refers to a composition when allowed to dry under ambient conditions (e.g., 23° C. and 50% relative humidity (RH)) on intact skin forms a continuous layer that does not flake off after simple flexing of the tissue.

"Hydrophobic" means a material that has a low roll-off angle for water droplets. The material generally has a static contact angle of water (θ) that is between 90° and 140°. Generally, a hydrophobic material or coating is characterized by a static contact angle of water of 90° or above.

"Normal skin flora" refers to resident skin flora present on the skin of a healthy person and often consists of predominantly of *Staphylococcus epidermidis*.

"Plasticizing agent" refers to additives that increase the plasticity or decrease the viscosity of a material. These are the substances which are added in order to alter their physical properties. These are either liquids with low volatility or may even be solids. They decrease the attraction between polymer chains to make them more flexible.

"Compatible" refers to plasticizing agents that: (1) exhibit no gross phase separation from the latent, over-tackified, adhesive when combined in the prescribed amounts; (2) once mixed with the latent, over-tackified, adhesive, do not significantly phase separate therefrom upon aging; and (3) function as a rheological modification agent for the latent, over-tackified, adhesive, such that the plasticized composition exhibits pressure sensitive properties as defined above.

"Polymer" includes homopolymers and copolymers and "copolymer" includes a polymer of any length (including oligomers) of two or more types of polymerizable monomers, and therefore includes terpolymers, tetrapolymers, etc., which can include random copolymers, block copolymers, or sequential copolymers.

"Polyol" includes compounds containing active hydrogen in accordance with the Zerevitanov test described by C. R. Noller, *Chemistry of Organic Compounds*, Chapter 6, pages 121-122 (1957). The term "polyol" further means a compound having an average functionality greater than 1, preferably greater than 1.8, and most preferably about 2.0 or greater but less than about 6, preferably less than about 4, and most preferably about 3 or less. It is understood to include compounds that have (i) alcohol groups on primary, secondary, and tertiary carbon atoms, (ii) primary and secondary amines, (iii) mercaptans, and (iv) mixtures of these functional groups.

"Pressure sensitive adhesive" typically includes materials (e.g., elastomers) that are either inherently tacky or that are tackified with the addition of tackifying resins. They can be defined by the Dahlquist criteria described in Handbook of Pressure Sensitive Adhesive Technology, D. Satas, $2^{rd}$ ed., page 172 (1989) at use temperatures. This criterion defines a good pressure sensitive adhesive as one having a 1 second creep compliance of greater than $1\times10^{-6}$ $cm^2$/dyne. Alternatively, since modulus is, to a first approximation, the inverse of compliance, pressure-sensitive adhesives may be defined as adhesives having a modulus of less than $1\times10^6$ dynes/$cm^2$. Another well-known means of identifying a pressure sensitive adhesive is that it is aggressively and permanently tacky at room temperature and firmly adheres to a variety of dissimilar surfaces upon mere contact without the need of more than finger or hand pressure as described in "Glossary of Terms Used in the Pressure Sensitive Tape Industry" provided by the Pressure Sensitive Tape Council, August, 1985;

"Topographical surface" refers to a surface having features such as depressions and elevations especially with reference to a description of an anatomical region or part.

"Wound" refers to an injury to mammalian tissue that involves breaking of a membrane such as the skin or mucosal surface usually with damage to underlying tissue arising from, but not limited to, a surgical incision, puncture, or laceration.

LIST OF ILLUSTRATIVE EMBODIMENTS

1. An article, comprising:
   a conformable backing having first and second opposed major surfaces and comprising a thermoplastic polymer selected from a group consisting of polyurethanes, polyesters, and combinations thereof, and the backing has a tensile strength of no greater than 60 grams per centimeter force at 25% elongation in a machine direction according to the Tensile and Elongation Test Method; and
   a hydrophobic adhesive disposed on a portion of the first major surface of the backing, the hydrophobic adhesive comprising a cationic, bioactive agent, a hydrophobic solubilizer capable of solubilizing at least part of the bioactive agent, and a hydrophobic plasticizing agent having a weight average molecular weight of above 1500.
2. The article of embodiment 1, wherein the thermoplastic polymer is polyurethane.
3. The article of embodiment 2, wherein the thermoplastic polymer is an polyether-based thermoplastic polyurethane.
4. The article of embodiment 3, wherein the polyether-based thermoplastic polyurethane comprises aromatic groups.
5. The article of embodiment 2, wherein the thermoplastic polymer is a polyester-based thermoplastic polyurethane.
6. The article of any of embodiments 1 to 5, wherein the backing is a synthetic film backing arranged in a continuous layer.
7. The article of any of embodiments 1 to 5, wherein the backing has an average thickness from 0.5 to 2 mils.
8. The article of any of embodiments 1 to 7, wherein the backing comprises a bioactive agent.

8a. The article of any of embodiments 1 to 8, wherein the backing has substantially equivalent properties to a homopolymer under the trade designation Elastolan ET870.

8b. The article of any of embodiments 1 to 8a, wherein the backing has a Young's modulus of between 8 and 10 MPa (inclusive).

9. The article of any of embodiments 1 to 7, wherein 5 to 10 grains of adhesive are disposed on the backing per 30 square inches (16.5 to 33.5 g/$m^2$, inclusive).

10. The article of embodiment 9, wherein 6 to 9 grains of adhesive are disposed on the backing per 30 square inches (20 to 30 g/$m^2$, inclusive).
11. The article of embodiment 13, wherein 5 to 8 grains of adhesive (inclusive) are disposed on the backing per 30 square inches (16.5 to 26.8 g/$m^2$, inclusive).
12. The article of any of embodiments 1 to 5, wherein the thermoplastic polymer has an ultimate elongation of no greater than 700%.
13. The article of any of embodiments 1 to 9, wherein the adhesive is comprises a bioreactive agent.
14. The article of any of embodiments 1 to 13, wherein the adhesive is hydrophobic.
15. The article of any of embodiments 1 to 14, wherein the adhesive is a pressure sensitive adhesive.
16. The article of embodiment 15, wherein the pressure sensitive adhesive comprises:
    a (meth)acrylic copolymer comprising a crosslinked reaction product of a curable composition comprising a (meth)acrylic precursor that is an at least partially polymerized reaction product of a monovalent monomer mixture comprising:
    (1) a first monomer having a formula of $CH_2{=}C(R^1){-}(CO){-}OR^2$, where $R^1$ is hydrogen or a methyl group, and $R^2$ is an alkyl, heteroalkyl, alkenyl, or aryl group;
    (2) a second monomer that is a vinyl monomer expressed by

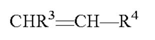

$CHR^3{=}CH{-}R^4$ wherein $R^3$ is hydrogen or a methyl group.
17. The article of embodiment 16, wherein $R^4$ is an acetate ester group.
18. The article of embodiment 17, wherein the second monomer is vinyl acetate.
19. The article of embodiment 16, wherein $R^4$ is an amide group expressed by $N(R^5)R^6$ where $R^5$ and $R^6$ are selected from hydrogen and linear or branched alkyl groups having a carbon number of 1 to 4, wherein $R^5$ and $R^6$ are not both hydrogen at the same time.
20. The article of embodiment 19, wherein $R^4$ is a cyclic amide monomer.
21. The article of embodiment 16, wherein $R^2$ of the first monomer is an alkyl group having 1 to 14 carbon atoms.
22. The article of embodiment 21, wherein $R^2$ of the first monomer is an alkyl group having 1 to 12 carbon atoms.
23. The article of embodiment 22, wherein $R^2$ of the first monomer is an alkyl group having 7 to 9 carbon atoms.
24. The article of embodiment 23, wherein $R^2$ of the first monomer is an alkyl group having 8 carbon atoms.
25. The article of any of embodiments 21 to 24, wherein $R^2$ of the first monomer is a linear alkyl group.
26. The article of any of embodiments 21 to 25, wherein $R^2$ of the first monomer is a branched alkyl group.
27. The article of any of embodiments 21 to 26, wherein $R^2$ of the first monomer is an aliphatic alkyl group.
28. The article of embodiment 27, wherein $R^2$ of the first monomer is an cycloaliphatic alkyl group.
29. The article of any of embodiments 21 to 28, wherein the first monomer is selected from a group consisting of: isooctyl acrylate, 2-ethylhexyl acrylate, lauryl acrylate, isobutyl acrylate monomers, and combinations thereof.
30. The article of any of embodiments 1 to 29, wherein the second monomer is selected from a group consisting of vinyl acetate, N-vinylcaprolactam (NVC), N-vinylpyrrolidone (NVP), N,N-dimethylacrylamide (nnDMA), N,N-diethylacrylamide (nnDEA), and N,N-dimethylmethacrylamide, and combinations thereof.
31. The article of any of embodiments 1 to 30, wherein the solubilizer is a monoacylglyceride, a diol, ester, or combinations thereof.
32. The article of embodiment 31, wherein an acyl group of the monoacylglyceride is a C8 to C18 acyl group.
33. The article of embodiment 32, wherein the monoacylglyceride comprises two vicinal hydrogen-bonding groups.
34. The article of any of embodiments 32 to 33, wherein the monoacylglyceride is selected from the group consisting of glycerol monocaprylate, glycerol monolaurate, glycerol monoisostearate, glycerol monooleate, and combinations thereof.
35. The article of any of embodiments 16 to 34, wherein the (meth)acrylic copolymer is between 75 and 85 wt. % (inclusive) of the adhesive.
36. The article of embodiment 35, wherein the (meth)acrylic copolymer is between 75 and 80 wt. % (inclusive) of the adhesive.
37. The article of any of embodiments 16 to 36, wherein the monovalent monomer mixture comprises 80 to 90 wt. % (inclusive) of the first monomer and 10 to 20 wt. % (inclusive) of the second monomer.
38. The article of any of embodiments 16 to 37, wherein 1 wt. % to 3 wt. % (inclusive) of the bioactive agent is present in the adhesive.
39. The article of any of embodiments 16 to 38, wherein 8 to 11 wt. % (inclusive) of the solubilizer is present in the adhesive.
40. The article of any of embodiments 16 to 39, wherein the adhesive comprises 8 to 11 wt. % (inclusive) of a hydrophobic plasticizing agent.
41. The article of any of embodiments 1 to 40, wherein the hydrophobic plasticizing agent has the capability to lower or reduce a glass transition temperature of the adhesive sufficient for the adhesive to meet the Dahlquist criterion.
42. The article of embodiment 41, wherein the adhesive has a modulus of elasticity of no greater than 0.3 MegaPascals (MPa).
43. The article of embodiment 42, wherein the adhesive has a modulus of elasticity of no greater than 0.1 MPa.
44. The article of any of embodiments 1 to 43, wherein the hydrophobic plasticizing agent has an HLB from 1 to 2.
45. The article of any of the embodiments 16 to 40, wherein the adhesive comprises a dye.
46. The article of any of embodiments 1 to 45, further comprising a support layer disposed on the second major surface of the backing.
47. The article of any of embodiments 1 to 46, further comprising a release liner disposed on the adhesive.
48. The article of any of embodiments 1 to 47, wherein a material formed from the thermoplastic polymer has a shore A hardness rating of no greater than 75.
49. A system, comprising:
    the article of any of embodiments 1 to 48, wherein the article has a first side and a second side;
    an antiseptic solution comprising alcohol, wherein when the first side of the article contacts a layer of the antiseptic solution applied to a topographical surface, a frequency of lift of any portion of the article is no greater than 80% out of a statistically relevant sample set of topographical surfaces.

50. The system of embodiment 49, wherein the antiseptic solution is a film-forming composition comprising a bioactive agent.
51. The system of embodiment 49, wherein the topographical surface is an anatomical surface.
52. The system of embodiment 49 wherein the anatomical surface is a human knee.
53. The system of any of embodiments 49 to 52, wherein no greater than 7.5%, or more preferably, no greater than 5.8%, or most preferably, no greater than 5.0% of a surface area of the article lifts from the topographical surface.
54. The system of embodiment 49, wherein the film-forming composition comprises a polymer.
55. The system of embodiment 49, wherein the bioactive agent comprises iodine.
56. The system of embodiment 49, wherein the bioactive agent comprises a chlorhexidine salt.
57. The system of embodiment 49, wherein the surface is mammalian skin.
58. The system of embodiment 49, wherein the topographical surface is a joint of an adult human.
59. A method, comprising:
providing a bioactive agent;
admixing the (meth)acrylic copolymer of any of the preceding embodiments, bioactive agent of any of the preceding embodiments, solubilizer of any of the preceding embodiments, and plasticizing agent of any of the preceding embodiments to form an adhesive composition;
depositing the adhesive composition onto a conformable backing to form an article, the backing having first and second opposed major surfaces and comprising a thermoplastic polymer selected from a group consisting of polyurethanes, polyesters, and combinations thereof, wherein a material formed from the thermoplastic polymer has a shore A hardness rating of greater than 70, and the backing has a tensile strength of no greater than 60 grams per centimeter force at 25% elongation in the machine direction.
60. The method of embodiment 59, further comprising: conditioning the bioactive agent.
61. The method of embodiment 59, wherein conditioning the bioactive agent includes removing water from the bioactive agent.
62. The method of embodiment 61, wherein removing the water comprises lyophilizing the bioactive agent.
63. The method of any of embodiments 59 to 62, further comprising: applying the article to the patient.
64. A method, comprising:
applying a film-forming composition to a surface of a patient;
applying the article of any of embodiments 1 to 48 to the surface;
allowing no greater than 7.5% of a surface area of the article to lift from the surface as measured using the knee model.
65. The method of embodiment 64, wherein applying the article comprises:
removing the release liner from the article;
gripping portions adjacent to the first and second side edges of the film;
positioning the article over a surgical site with the adhesive directed toward the surgical site on the patient's body; and
conformably adhering the article over the surgical site.

What is claimed is:

1. An article, comprising:
a conformable backing, comprising:
a first major surface;
a second major surface opposed to the first major surface; and
a thermoplastic polymer selected from the group consisting of polyurethanes, polyesters, and combinations thereof,
wherein the conformable backing has a tensile strength of no greater than 50 grams force per centimeter at 25% elongation in a machine direction according to the Tensile and Elongation Test Method; and
a hydrophobic adhesive disposed on a portion of the first major surface of the conformable backing, wherein the hydrophobic adhesive is a pressure sensitive adhesive comprising:
75 wt. % to 85 wt. % of a (meth)acrylic copolymer;
1 wt. % to 3 wt. % of a cationic bioactive agent;
8 wt. % to 11 wt. % of a hydrophobic solubilizer capable of solubilizing at least part of the bioactive agent; and
8 wt. % to 11 wt. % of a hydrophobic plasticizing agent having a weight average molecular weight of above 1500,
wherein the article is configured to reduce drape lift.

2. The article of claim 1, wherein the thermoplastic polymer is polyurethane.

3. The article of claim 2, wherein the thermoplastic polymer is a polyether-based thermoplastic polyurethane.

4. The article of claim 3, wherein the polyether-based thermoplastic polyurethane comprises aromatic groups.

5. The article of claim 2, wherein the polyurethane is a polyester-based thermoplastic polyurethane.

6. The article of claim 1, wherein the conformable backing is a synthetic film backing arranged in a continuous layer.

7. The article of claim 1, wherein the conformable backing has an average thickness in a range of 0.5 mils to 2 mils.

8. The article of claim 1, wherein 16.5 to 33.5 $g/m^2$ of the hydrophobic adhesive are disposed on the conformable backing.

9. The article of claim 1, wherein the (meth)acrylic copolymer comprises a crosslinked reaction product of a curable composition comprising a (meth)acrylic precursor that is an at least partially polymerized reaction product of a monovalent monomer mixture comprising:
(1) a first monomer having a formula of $CH_2{=}C(R^1){-}(CO){-}OR^2$, where $R^1$ is hydrogen or a methyl group, and $R^2$ is an alkyl, heteroalkyl, alkenyl, or aryl group; and
(2) a second monomer that is a vinyl monomer expressed by

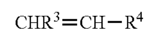

wherein $R^3$ is hydrogen or a methyl group, wherein $R^4$ is an acetate ester group, wherein the second monomer is vinyl acetate, and wherein $R^2$ of the first monomer is an alkyl group having 7 to 9 carbon atoms.

10. The article of claim 9, wherein the first monomer is selected from the group consisting of isooctyl acrylate, 2-ethylhexyl acrylate, lauryl acrylate, isobutyl acrylate monomers, and combinations thereof, and wherein the second monomer is selected from the group consisting of vinyl acetate, N-vinylcaprolactam (NVC), N-vinylpyrrolidone (NVP), N,N-dimethylacrylamide (nnDMA), N,N-diethylacrylamide (nnDEA), and N,N-dimethylmethacrylamide, and combinations thereof.

11. The article of claim 1, wherein the hydrophobic adhesive comprises a solubilizer selected from the group consisting of a monoacylglyceride, a diol, ester, and combinations thereof.

12. The article of claim 1, wherein the hydrophobic plasticizing agent is configured to lower a glass transition temperature of the hydrophobic adhesive sufficient for the hydrophobic adhesive to meet the Dahlquist criterion.

13. The article of claim 1, further comprising a support layer disposed on the second major surface of the conformable backing.

14. The article of claim 1, wherein the article exhibits a geometric mean of lifted area of less than 1200 mm2.

15. The article of claim 1, wherein the article is an incise drape.

* * * * *